United States Patent [19]

Sugiyama et al.

[11] Patent Number: 5,770,715
[45] Date of Patent: Jun. 23, 1998

[54] HAMMERHEAD-LIKE NUCLEIC ACID ANALOGUES AND THEIR SYNTHESIS

[75] Inventors: Hiroshi Sugiyama; Ken Hatano; Isao Saito, all of Kyoto; Takayoshi Uchida, Ibaraki; Yoko Matsuda, Ibaraki; Kiyoshi Uchida, Ibaraki, all of Japan

[73] Assignee: Toagosei Co., Ltd., Tokyo, Japan

[21] Appl. No.: 618,960

[22] Filed: Mar. 20, 1996

[30] Foreign Application Priority Data

Mar. 22, 1995 [JP] Japan ..................................... 7-063188

[51] Int. Cl.$^6$ .................................................. C07H 21/00
[52] U.S. Cl. .................... 536/23.1; 536/25.34; 536/24.3; 536/24.5
[58] Field of Search ................................ 536/23.1, 25.34

[56] References Cited

FOREIGN PATENT DOCUMENTS 9501370  1/1995  WIPO.
9634109  10/1996  WIPO.

OTHER PUBLICATIONS

Manoharan, "Designer Antisense Oligonucleotides: Conjugation Chemistry and Functionality Placement," Ch. 17 in *Antisense Research and Applications*, Crooke & LeBleu (eds.), CRC Press, Inc., Boca Raton, FL, 1993, 579 pages, only pp. 303–349 supplied.

Sugiyama et al., "Catalytic Activities of Hammerhead Ribozymes With a Triterpenoid Linker Instead of Stem/Loop II," *FEBS Letters*, 392(3), 215–219 (Sep. 2, 1996).

Hirao, et al., *Most compact hairpin–turn structure exerted by a short DNA fragment, d(GCGAAGC) in solution: an extraordinarily stable structure resistant to nucleases and heat*, Nucleic Acids Research, 22(4):576, 1994.

Hirao, et al., *Stabilization of mRNA in an Escherichia coli cell–free translation system*, FEBS Letters, 321(2,3):169, Apr. 1993.

Khan and Coulson, *A novel method to stabilise antisense oligonucleotides against exonuclease degradation*, Nucleic Acids Research, 21(12):2957, 1993.

Akira Murakami, *Basic of Antisense Molecules*, Journal of Clinical and Experimental Medicine, 170(13):1994.

Tang, et al., *Self–stabilized antisense oligodeoxynucleotide phosphorothioates: properties and anti–HIV activity*, Nucleic Acids Research, 21(11):2729, 1993.

*Primary Examiner*—John Kight
*Assistant Examiner*—L. Eric Crane
*Attorney, Agent, or Firm*—Fish & Richardson, P.C.

[57] ABSTRACT

The present invention provides nucleic acid compounds which have a non-nucleic acid structure with ring skeleton to which two functional groups are bound with fixed state and are able to point to substantially the same direction, nucleic acid compounds which can form triple strands with third nucleotide chains, nucleic acid compounds which have improved permeability, and synthetic methods thereof.

15 Claims, 10 Drawing Sheets

FIG. I

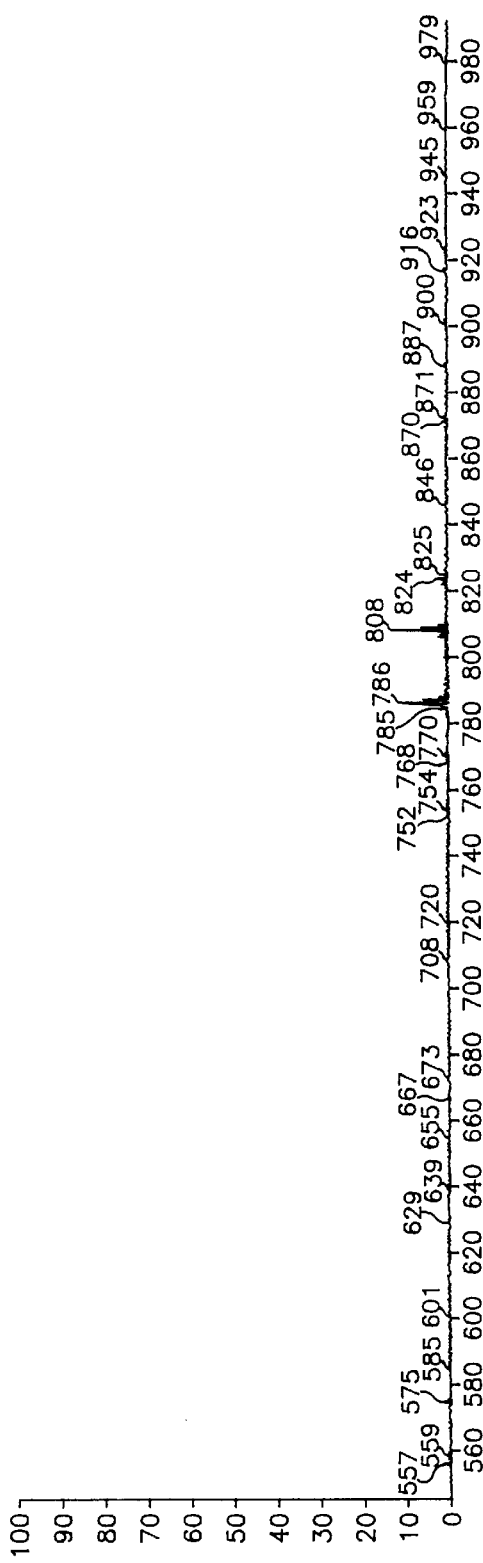
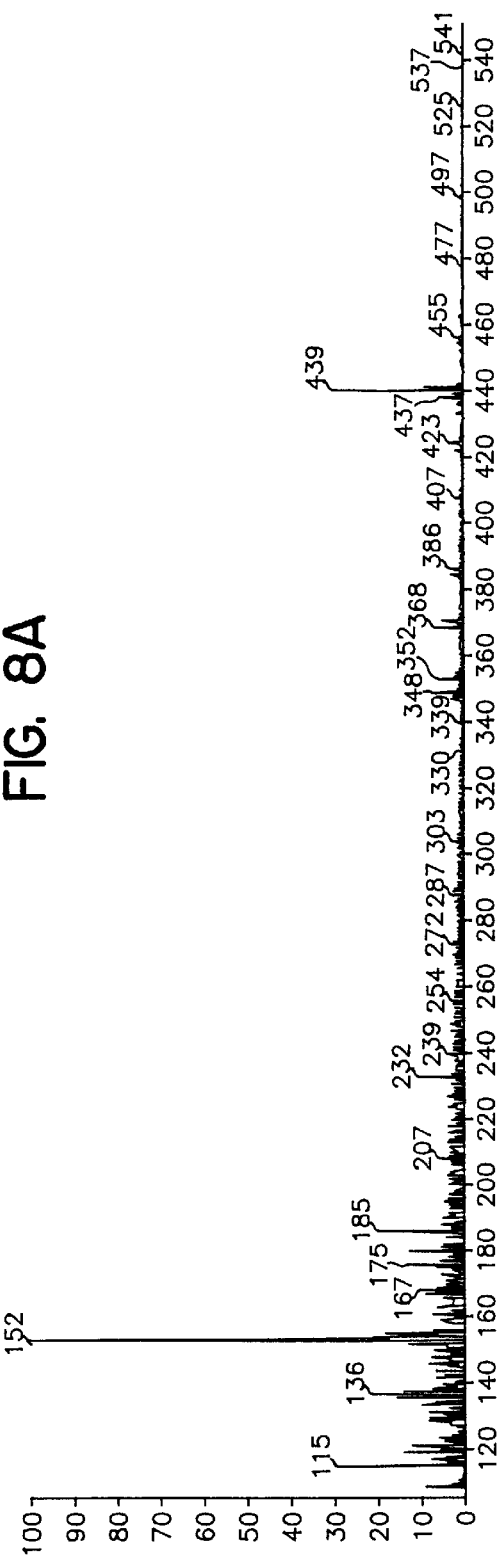
FIG. 8A
FIG. 8B

HAMMERHEAD-LIKE NUCLEIC ACID ANALOGUES AND THEIR SYNTHESIS

FIELD OF THE INVENTION

The present invention relates to nucleic acid compounds which promote formation of intramolecularly base-paired structure arising from two nucleotide chains of which sequences are substantially complementary to each other, compounds which have improved permeability, compounds which promote triple strand formation with the third nucleotide chain, their synthetic methods, and compounds which give the nucleic acid compounds.

BACKGROUND OF THE INVENTION

As nucleic acid compounds, various compounds are known: for instance, nucleic acid compounds which have enhanced hydrophobicity or nuclease resistance by modifying base, sugar, or phosphodiester part of nucleic acids; nucleic acid compounds which have functional groups such as hydrophobic groups, fluorescent groups, or charge neutralizing groups at the 5' or 3' terminus of the nucleic acids or other part thereof; nucleic acid compounds which have intercalating groups (E. Uhlmann and A. Peyman, *Chemical Reviews*, 90: 543–584(1990); F. Eckstein ed., *Oligonucleotides and Analogues—A Practical Approach*, IRL press (1991); J. F. Milligan et al., *Medicinal Chemistry*, 38: 1923–1937(1993)).

However, any compounds descried above do not promote formation of intramolecularly base-paired structure formed from two nucleotide chains of which sequences are substantially complementary to each other.

In addition, it is known the presence of neither compounds which have functional groups to form triple strands with the third nucleotide chain nor compounds which have hydrophobic functional groups between the two nucleotide chains when the compounds have such chains.

SUMMARY OF THE INVENTION

The present invention provides nucleic acid compounds which promote intramolecularly base-paired structure formed from complementary base sequences, compounds which promote triple strand formation with the third nucleotide chain, compounds which have improved permeability, their synthetic methods, and compounds which give the nucleic acid compounds.

The inventors of the present invention found nucleic acid compounds which promote formation of intramolecularly base-paired structure arising from two nucleotide chains of which sequences are substantially complementary to each other, using non-nucleic acid compounds having a certain structure, and completed the present invention.

The present invention provides nucleic acid compounds which have a ring-like structure, two functional groups, and a pair of nucleotide chains. These functional groups are bound to the ring-like skeleton with a fixed structure and are able to point to substantially the same direction. The nucleotide chains are bound through such functional groups, and they form the intramolecularly base-paired structure.

The present invention also provides methods to synthesize nucleic acid compounds having a ring skeletone wherein the compounds are characterized by a pair of complementary nucleotide chains bound to the rings through the functional groups.

Furthermore, the present invention is triterpenoid compounds which have non-nucleic acid structure with ring skeleton shown in the following chemical formula (1) or (2):

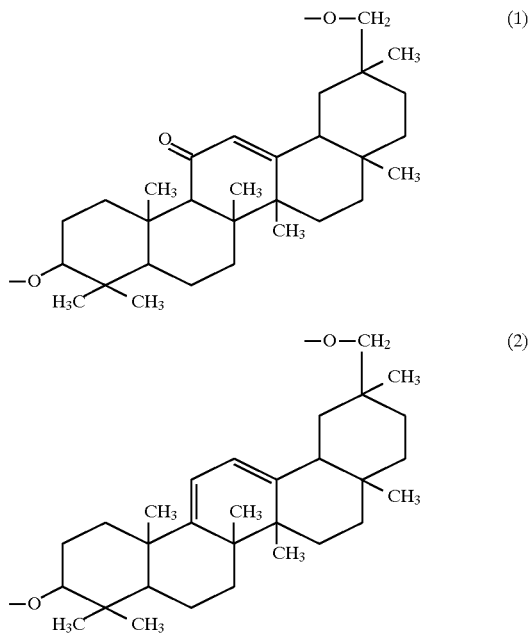

and the novel triterpenoid compounds of the present invention are shown in the following chemical formula (3) or (4):

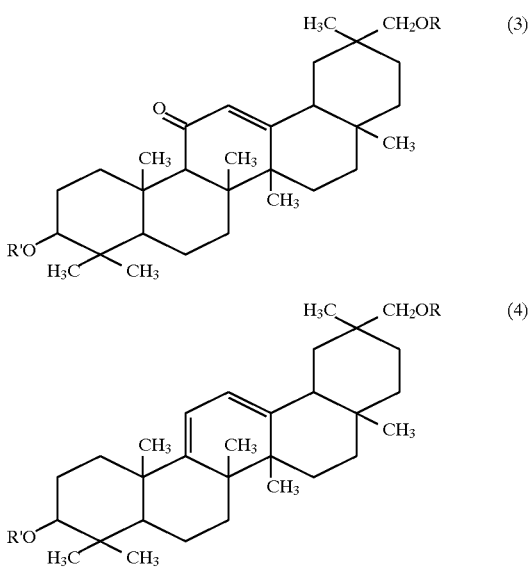

wherein both R and R' represent a hydrogen atom or a protecting group.

The present invention also provides novel phosphoramidite esters of the triterpenoid compounds shown in the following chemical formula(5) or (6):

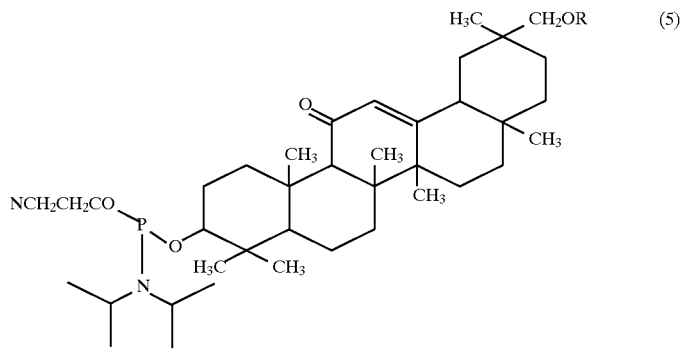
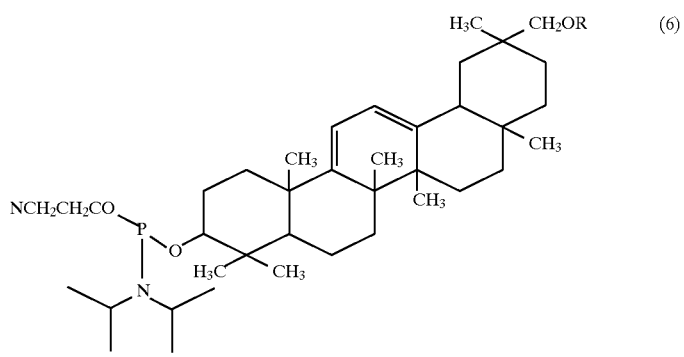
wherein R represents a hydrogen atom or a protecting group.
The present invention further provides thiophosphite esters of the triterpenoid compound shown in the following chemical formula(7) or (8):
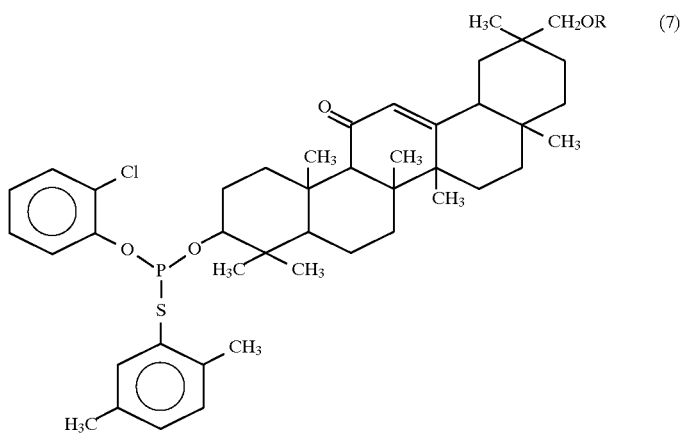

-continued

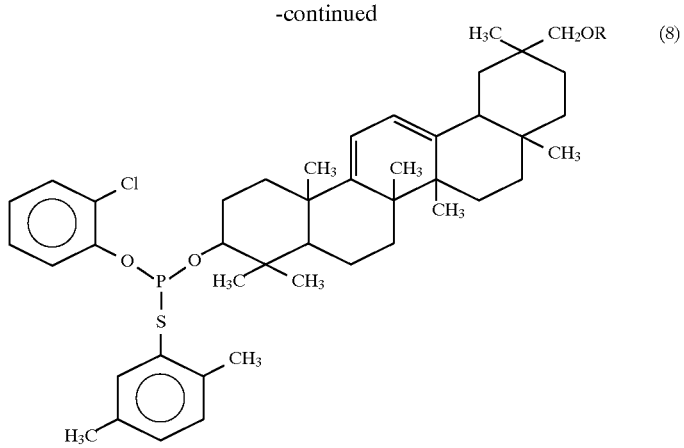

wherein R represents a hydrogen atom or a protecting group.

The present invention is described in detail herein below.

The nucleic acid compounds of the present invention have a non-nucleic acid structure with two functional groups and two nucleotide chains which are bound to the structure through the functional groups. Nucleotide chains having any DNA sequence may be employed; however, preferable are the chains which form double strands, or those which form triple strands in which one of the chains bound to the structure forms double strand with the third chain and another chain bound to that is bound to the double strand formed.

The third chain is defined as a nucleotide chain which is different from the nucleotide chains bound to the skeleton through the functional groups; the third chain is not bound to the structure, and its termini are free in general.

Since the structure has ring-like skeleton, the structure is referred to as the non-nucleic acid ring skeleton. Two functional groups are bound to the non-nucleic acid ring skeleton through 2 functional groups, and they are fixed so as to point to substantially the same direction. In general, since the distance between nucleotide chains forming complementary base pair or that among the chains forming triple strand is 0.8 to 1.2 nm, such distance between the functional groups in the present invention is preferable 0.6 to 1.4 nm, particularly 0.8 to 1.2 nm is preferable.

As such non-nucleic acid ring skeleton, a triterpenoid skeleton, a steroid skeleton, a condensed polycyclic skeleton, an adamantane skeleton, a polyalicyclic hydrocarbon skeleton, a skeleton having a hetero ring(s), a skeleton a having metal complex(es), or a skeleton derived from natural sources are given.

As the example of the triterpenoid skeleton, the compound shown in the following chemical formulae(1') and (2') are given.

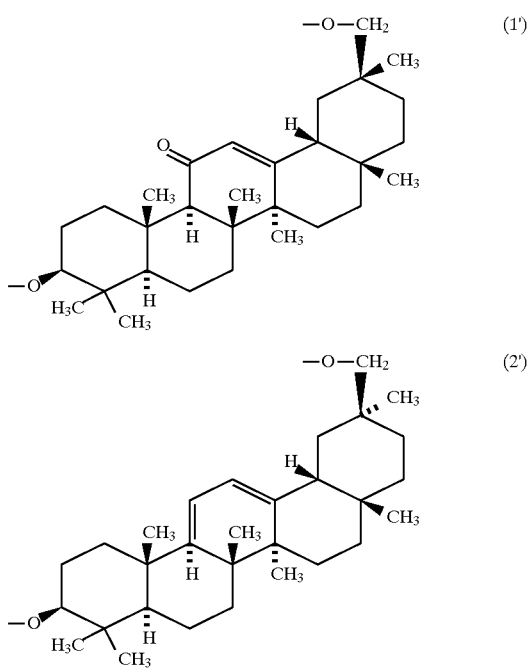

As other examples of such skeleton, the compound shown in the following chemical formula(9) or (10) are given. Both compounds shown in the formulae(9) and (10) have opposite stereo structures of hydrogen atom for D and E rings of the compound shown in the formulae(1') and (2'), respectively.

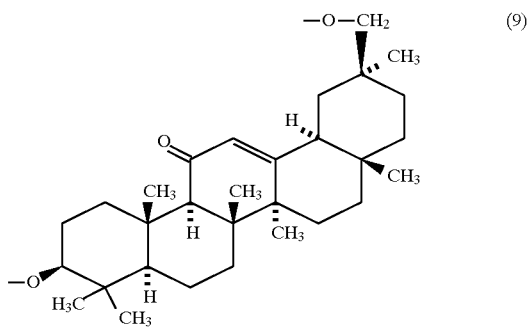

-continued

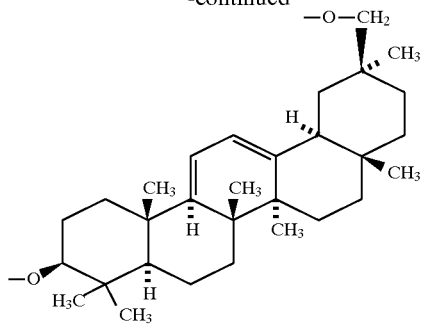
(10)

The nucleic acid compounds having the triterpenoid skeleton and two nucleotide chains, in particular, of which sequences are substantially complementary to each other, or nucleotide chains which can form triple strands with the third chain are synthesized according to the following steps:

(a) a commercially available compound, glycyrrhetinic acid shown in the following formula(11),

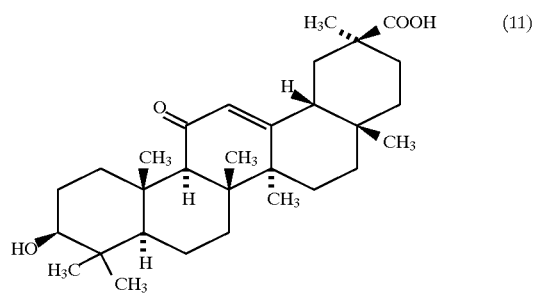
(11)

is esterified by using methanol. Briefly, glycyrrhetinic acid is dissolved in a sufficient amount of methanol, and refluxed with suitable amount of conc. sulfuric acid to esterify. Preferably, this esterification procedure is repeated at least twice. After that, methanol is removed by evaporation, and then the residue is loaded on a silica gel short column to obtain the compound shown in the following formula(12).

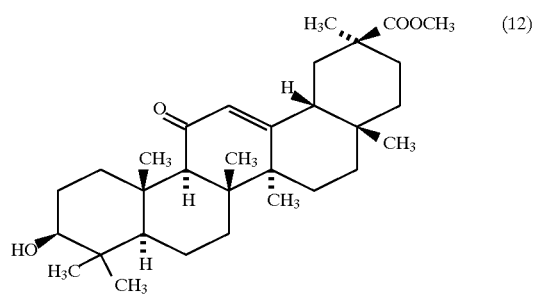
(12)

(b) The compound(12) obtained is reacted with diisobutylalminum(DIBAL). Briefly, the compound(12) is dissolved in a sufficient amount of a solvent such as methylene chloride in an atmosphere of nitrogen, and the mixture is cooled at −60° to −78° C. and DIBAL (1.5M DIBAL in toluene) is added; then the mixture is warmed up to room temperature, and stirred overnight at room temperature. The reaction is stopped by adding water of which volume is about ⅓ of methylene chloride used for dissolving the compound(12). The solvent in the reaction mixture is then removed by evaporation. Preferably, methylene chloride is added to the residue obtained after evaporation, and the residue is broken up and stirred well; then the solid, that is the broken residue, is filtrated and methylene chloride is removed by evaporation to obtain crude alcohol.

In the next step, the crude alcohol obtained is oxidized. Briefly, the crude alcohol obtained is dissolved in a solvent such as methylene chloride, and a suitable amount of $MnO_2$ is added, and the mixture is stirred overnight at room temperature. The solid obtained is filtrated, and the solvent is removed by evaporation; then the residue is purified by using preparative TLC and so forth. Thus, the compound(13) obtained is shown in the following formula, and the compound is referred to as compound (13).

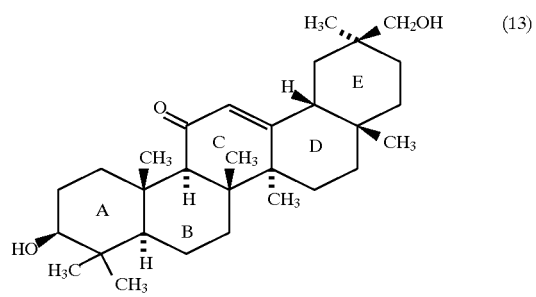
(13)

Both OH groups positioned at 3 which is secondary OH group on A ring and at 30 which is primary OH group at E ring can have substantially the same direction. Furthermore, since the distance between these OH groups are about 1.25 nm, this distance makes the complementary nucleotide chains form a complementary base-paired structure without any structural difficulties, or incorporate two nucleotide chains which can form triple strand with the third nucleotide chains intramolecularly.

The above-mentioned compound is also synthesized by using the following method.

(a') A commercially available compound, glycyrrhetinic acid shown in the following formula(11),

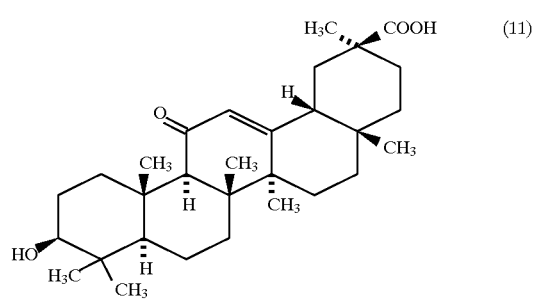
(11)

is reduced by using aluminum lithium hydride. Briefly, glycyrrhetinic acid is reduced in anhydrous tetrahydrofuran by using aluminum lithium hydride, preferably overnight with stirring. Excess aluminum lithium hydride is decomposed by using both water and NaOH, and then the solution is concentrated to obtain white crystalline. Since the crystalline is crude, it is recrystallized in methanol to obtain the compound shown in the following chemical formula(14). The compound is referred to as the compound(14).

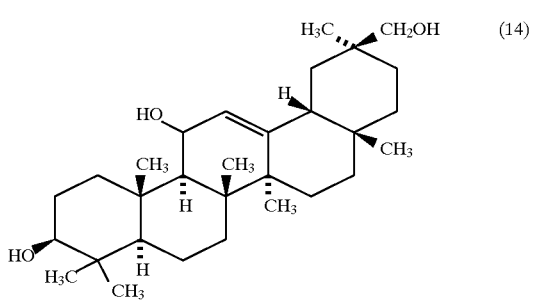

(b') The compound(14) obtained is oxidized. Briefly, the compound(14) is dissolved in a sufficient amount of a solvent such as methylene chloride, and a suitable amount of $MnO_2$ is added, and the mixture is stirred overnight at room temperature. The solid obtained is filtrated, and the solvent is removed by evaporation; then the residue is purified by using preparative TLC and so forth. Thus, the compound(13) obtained is shown in the following formula, and the compound is referred to as the compound (13).

In this (b') step, the compound (14) may be dehydrated, and the dehydration step is referred to as the step(b''). Briefly, the compound(14) is dissolved in a mixture of methanol and HCl, and stirred for 1 hr at room temperature. Then the solution is concentrated to dryness to obtain white crystalline. The crystalline is recrystallized in methanol to obtain the compound shown in the following chemical formula(15).

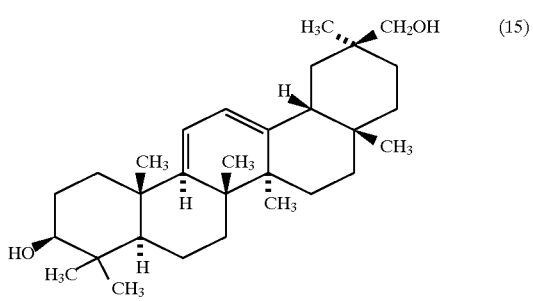

(c) A protecting group is introduced into the OH group at 30 on E ring of the compound(13) or (15) obtained to protect the OH group. Various known protecting group can be employed as such protecting groups; concretely, trityl group, methoxytrityl group, dimethoxytrityl group, acetyl group, benzoyl group, p-anisoyl group and tributyryl groups are given. As an example, we show a reaction with dimethoxytrityl group below.

Either the compound(13) or (15) is reacted with 4,4'-dimethoxytrityl chloride(DMTrCl). Briefly, either the compound(13) or (15) is dissolved in dried pyridine, and then evaporated to dryness. Preferably, the procedure to dry compound(13) or (15) is repeated 3 or 4 times. The dried compound(13) or (15) is dissolved in dried pyridine again, and 4,4'-dimethoxytrityl chloride, dimethylaminopyridine, and triethylamine are added to the solution. After that, the mixture is stirred overnight in an atmosphere of nitrogen at room temperature. As another way, DMTrCl is added to the dried pyridine containing either the compound(13) or (15), and the solution is stirred about 6 hr in an atmosphere of nitrogen at room temperature. In both ways described above, dimethoxytrityl chloride is preferably added about 2 equivalent to the compound(13) or (15). Dimethylaminopyridine is preferably added about 0.01 equivalent and triethylamine is about 1.5 equivalent to them. The compound obtained is partitioned by using ethyl acetate-water, and the organic layer containing ethyl acetate is dried on sodium sulfate anhydride. After that, ethyl acetate is removed by evaporation to purify the compound obtained. The compound can be purified by using silica gel columns. The compound obtained is shown in the either following chemical formula (3') or (4'),

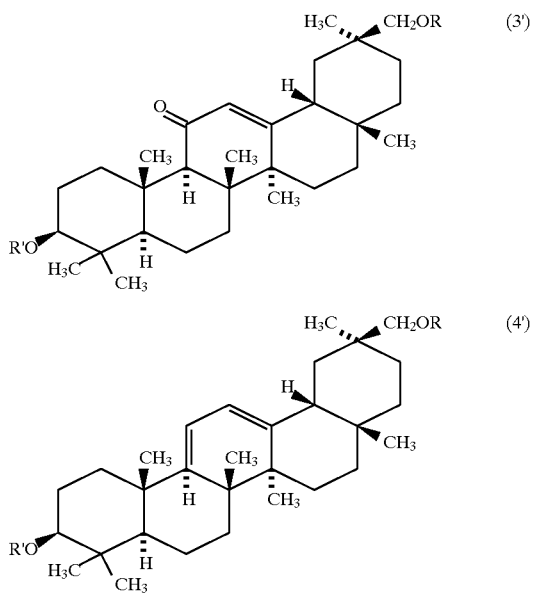

wherein R represents DMTr, and R' does a hydrogen atom. Thus compound obtained is referred to as the compounds(3') and (4'), respectively.

(d) The compound obtained(3') or (4') is reacted with a phosphoramidite, for example, 2-cyanoethyl-N,N,N',N'-tetraisopropylphosphoramidite, which has the following chemical formula(16).

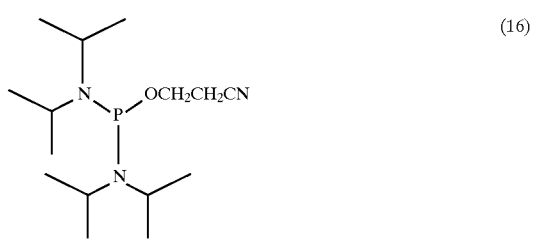

Briefly, the compound(3') or (4') is dissolved in dried acetonitrile and evaporated to dryness. Preferably, this drying procedure is repeated a couple of times. The compound (3') or (4') dried is dissolved in acetonitrile. Then both 2-cyanoethyl-N,N,N',N'-tetraisopropylphosphoramidite and tetrazole are added to the solution to react about one night. Preferably, 2-cyanoethyl-N,N,N',N'-tetraisopropyl phosphoramidite is added about 1.1 equivalent of either the compound(3') or (4'), and tetrazole is about 1.1 equivalent of it.

The compound obtained is partitioned by using ethyl acetate-saturated sodium hydrogen carbonate, and the ethyl acetate layer is dried on sodium sulfate anhydride; then the layer is evaporated to concentrate. The compound obtained has the following chemical formula(5') or (6'),

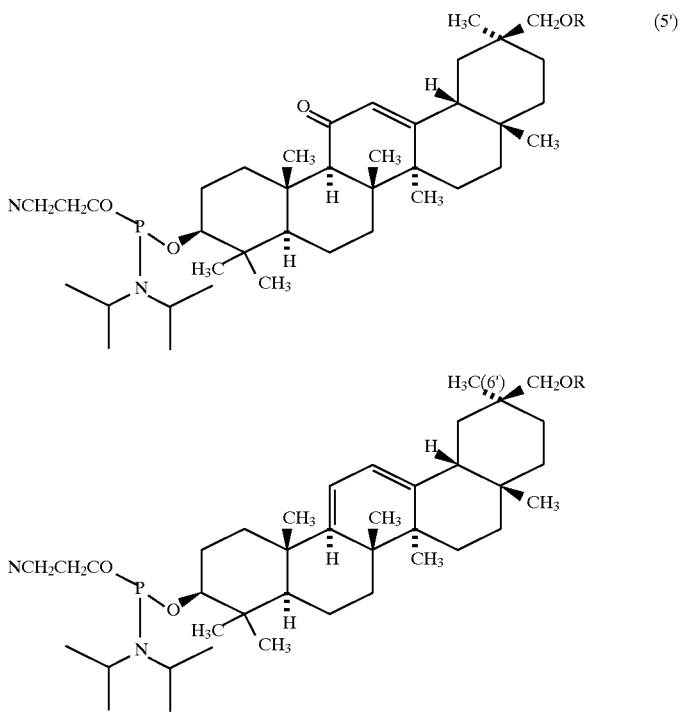

(5')

wherein R represents DMTr. The compounds obtained are referred to as the compound(5') and (6'), respectively.

(e) Finally, the compound (5') or (6') obtained is dissolved in a solvent, for example, acetonitrile-methylene chloride. Then the compound(5') or (6') is bound to nucleotide chains by using a DNA or RNA synthesizer. The nucleotide chain may be bound to the compound(5') or (6') in desirable stage, for example, at the stage that the synthesis of first nucleotide chain of two is finished and then other nucleotides are bound to that.

As another procedure, the synthesis is performed similarly to the procedures described as (a) and (b), in which (b') or (b") can be employed instead of (b), to obtain either the compound(13) or (15). The compound(13) or (15) is dissolved in chloroform. Then, 2-chlorophenoxy-2,5-dimethylthiochlorophosphine having the following chemical formula(17)

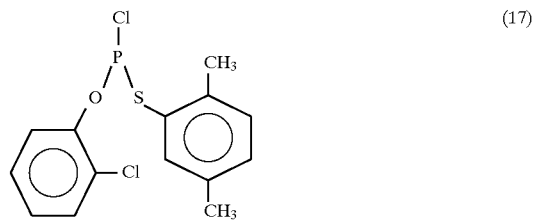

(17)

is added to the solution to obtain the compound having the following chemical formula(7') or (8'),

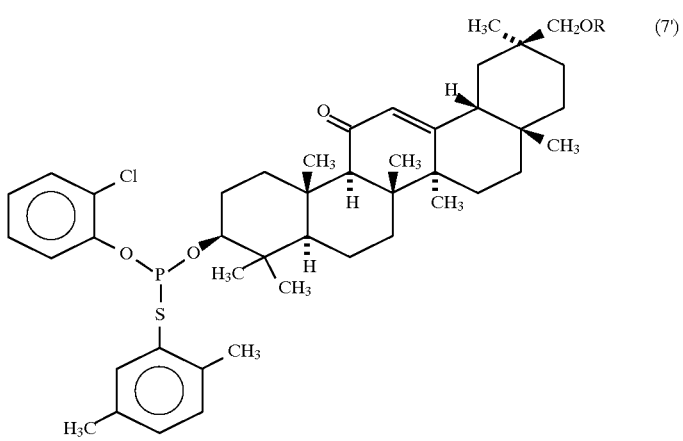

(7')

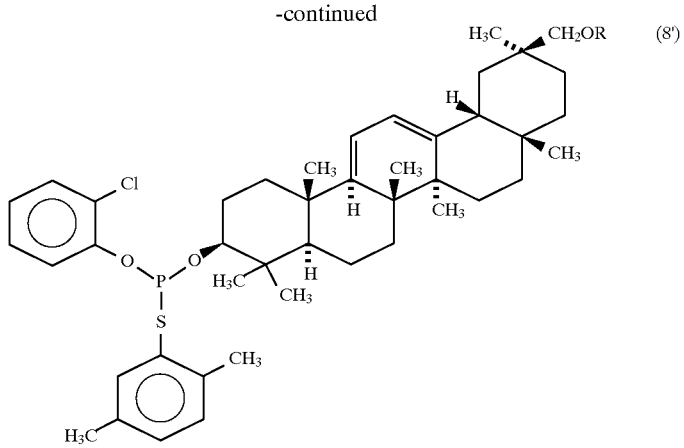

(8')

wherein, R represents DMTr. The compound obtained is referred to as the compounds(7') and (8'), respectively. After the compound(7') or (8') is obtained, the nucleotide chains are bound to the compound(7') or (8') as described above.

The functional groups in DNA chains, RNA chains, or nucleic acid compounds obtained above are protected respectively when they are synthesized to avoid undesirable reaction. Such nucleic acids compounds obtained are deblocked by using a known procedure and purified by a high performance liquid chromatography (HPLC) with packing materials for the reverse phase separation or the ion exchange separation, a convenient column like Sep Pack, or other procedure for compound analysis.

The reverse phase HPLC purification is performed by using, for example, a $C_{18}$ column (WAKO PURE CHEMICAL) and as an elution buffer, either 0.05M triethylammonium acetate buffer(pH 7.0) or 0.05M ammonium formate buffer with increasing amount of acetonitrile.

In EXAMPLES of the present invention, the phosphoramidite method can be employed, because phosphoramidite is used for the compound synthesis. The phosphoramidite method is defined as the synthetic method for nucleic acid related compounds such as oligodeoxyribonucleotides or oligoribonucleotides; in this method, phosphoroamidite reagents with protecting group of cyanoethyl at the 3'-termini of modified deoxyribonucleotides or modified ribonucleotides are condensed to 5'-termini of other nucleotides such as modified deoxyribonucleotides, modified ribonucleotides, oligomers of modified deoxyribonucleotides, oligomers of modified ribonucleotides and so forth.

The phosphoramidite method can be performed by using 381A DNA synthesizer or 394 DNA/RNA synthesizer(both produced by APPLIED BIOSYSTEMS), and referring the protocol provided by APPLIED BIOSYSTEMS or F. Eckstein ed. *Oligonucleotides and Analogues—A Practical Approach,* IRL Press(1991).

The nucleic acid compounds having the same stereostructure of OH groups on the compounds described above are also obtained by employing the thiophosphite method by using thiophosphite.

The compound thus obtained are shown in the following chemical structure(18a) or (18b), and they are referred to as the compounds(18a) and (18b), respectively,

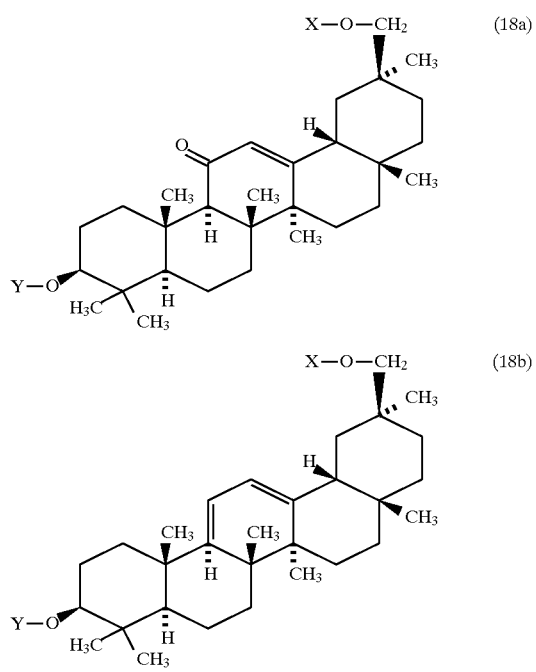

wherein X and Y represent complementary nucleotide chains including DNA chains, RNA chains, or nucleotide chains which can form triple strand with the third nucleotide. Any kind of DNA, RNA or the nucleotide chains described above may be employed if they are complementary each other, or they can form triple strand with the third nucleotide chain. Their sequences are not limited.

In the nucleic acid compound, both X and Y are DNA chains, RNA chains, nucleotide chains containing both DNA and RNA, or modified thereof which are modified such as phosphorthioate. They can form double strand or triple strand, and are a certain spatial location. The spatial location of such nucleotide chains are defined by the compound having the skeleton(1) or (2) bound to both termini of both X and Y. That is, the compound having the skeleton(1) or (2) corresponds to a loop part in a so-called hairpin structure formed in RNA and so forth. The nucleic acid compounds having such skeleton(1) or (2) have excellent permeability.

Synthetic methods for nucleic acid compounds having such skeleton shown in the chemical formula(1) or (2) are explained as examples. However, the synthetic methods for the compounds of the present invention are not limited to that described above. Accordingly, in order to synthesize the compounds of the present invention which can promote to form intramolecular complementary base-paired structure, the compounds which promote to form the triple strand with the third oligonucleotide chain, and those which have excellent permeability, various compounds can be employed by using other methods.

Since the compounds of the present invention described above are incorporated into cells easily due to its improved permeability, they give an excellent antisense nucleic acid effect and can use as pharmaceuticals or diagnostics. Particularly, they are available for pharmaceuticals or diagnostics which are required high nuclease resistance, when they have modified phosphodiester bond between bases. Furthermore, the present invention can apply for inhibiting the expression of genes which cause diseases, as a modification of antisense method, when the compounds have two nucleotide chains which can form triple strand with the third nucleotide chain.

BRIEF DESCRIPTION OF DRAWINGS

FIG. 8 shows the FAB (positive) spectrum of the compound with the chemical formula(22).

EXAMPLES

The present invention is explained in detail by using EXAMPLES herein below; however, the present invention is not limited to such EXAMPLES.

(Example 1)

(a) Five g of 18β-glycyrrhetinic acid (G1,010-5, 10.6 mmol, ALDRICH CHEMICAL) is dissolved in 200 ml of methanol. Four ml of conc. sulfuric acid is added to the solution, and then the mixture is refluxed for 3 hours. Another 4 ml of conc. sulfuric acid is added to the mixture, and refluxed further for 3 hours. Methanol is removed by evaporation, and the residue is applied on the silica gel short column (100 g of silica gel(Wako-gel 200), hexane/ethyl acetate=1/4(v/v)). The rough product of methyl ester having the following chemical structure(12) is obtained.

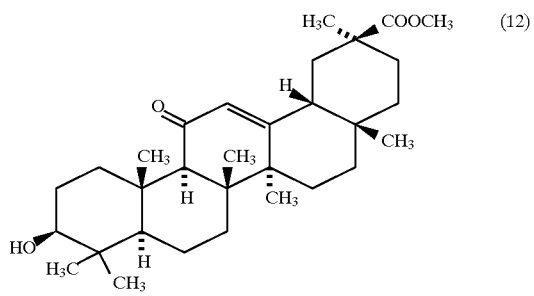

Figure 1:
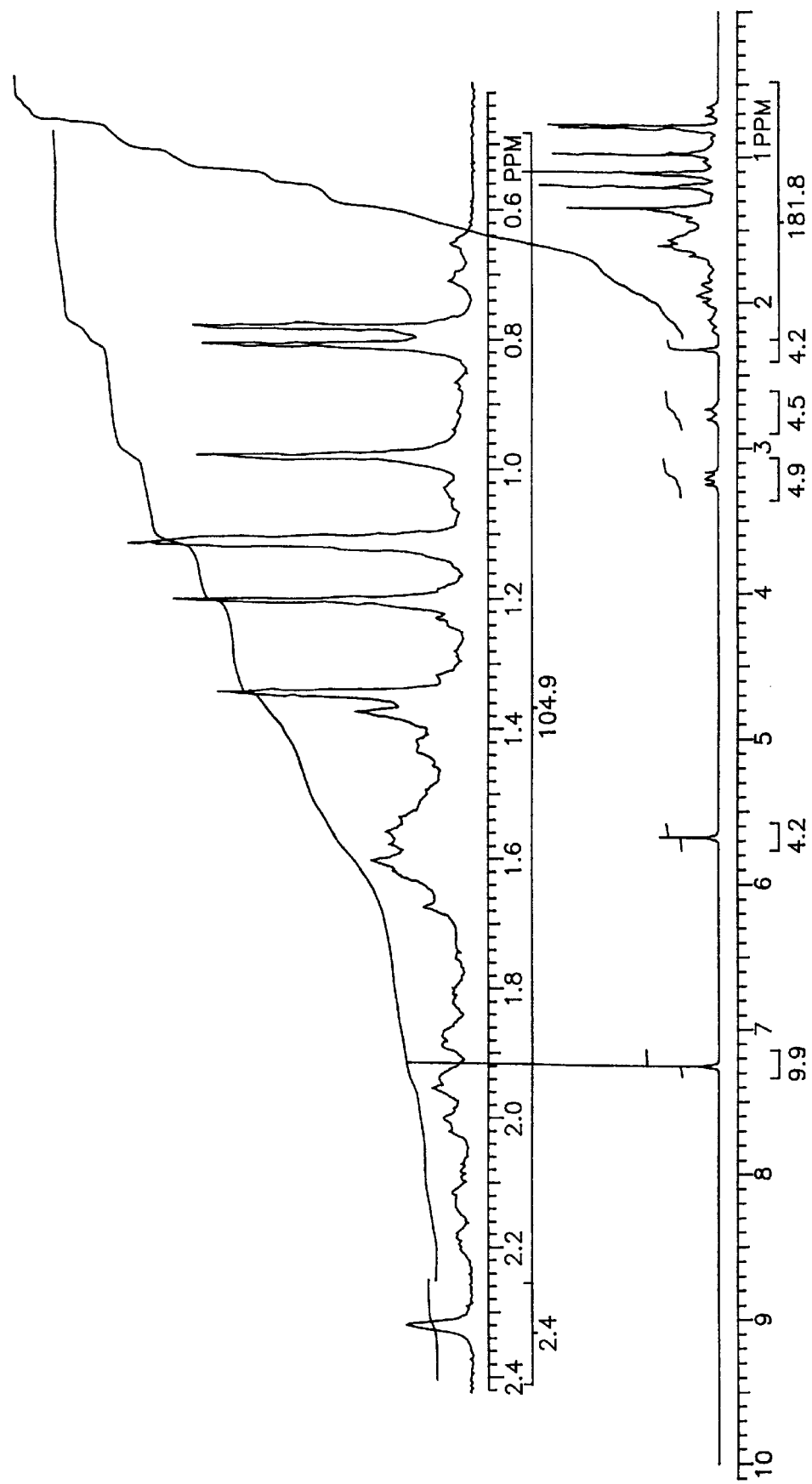
FIG. 1 shows the $^1$H NMR (CDCl$_3$, 200 MHz) spectrum of glycyrrhetinic acid.
Figure 2:
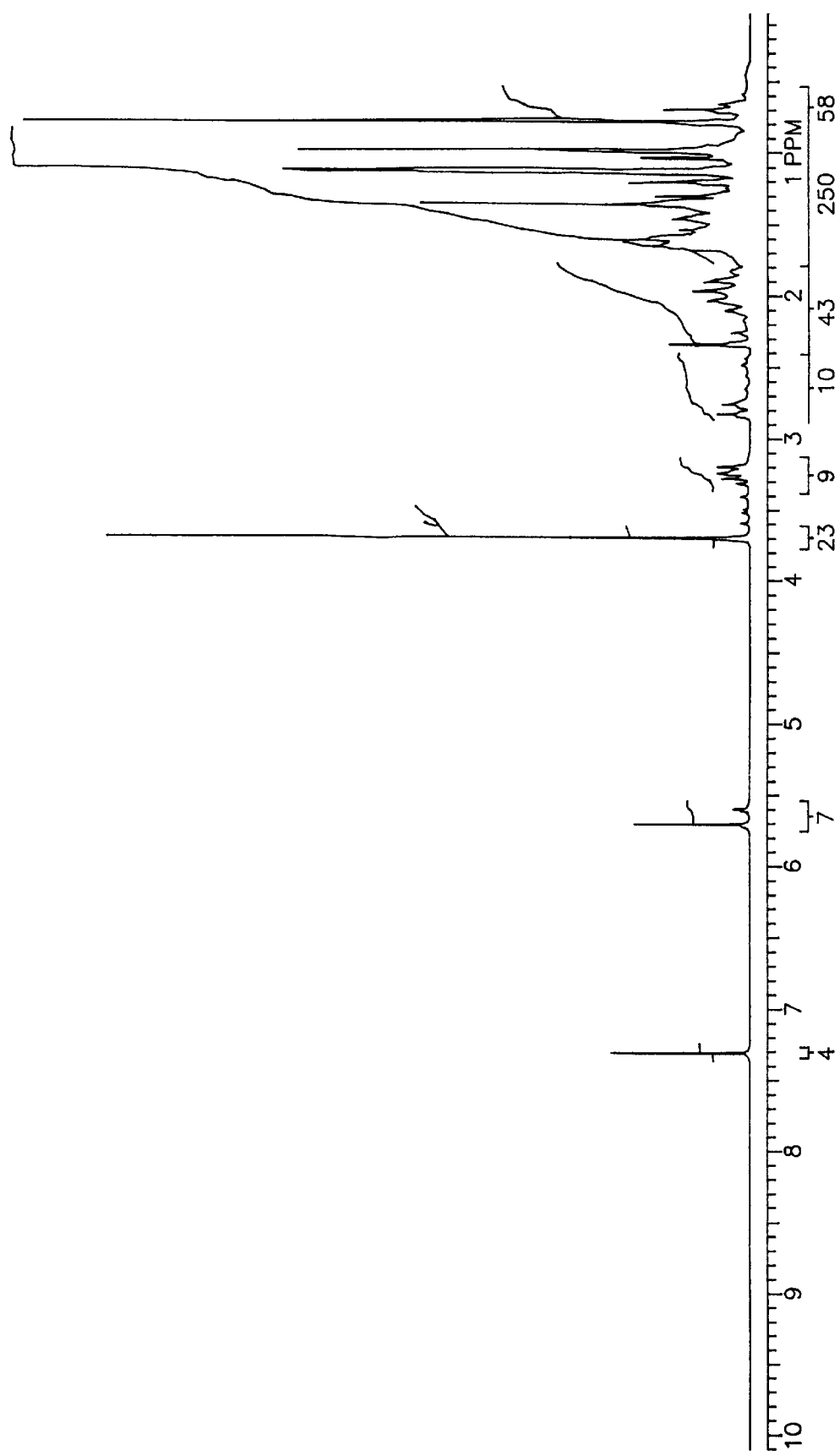
FIG. 2 shows the $^1$H NMR (CDCl$_3$, 200 MHz) spectrum of the compound with chemical formula(12).

The weight of the compound(12) obtained is 4.0 g, and the yield is 77.7%. The $^1$H NMR spectrum(CDCl$_3$, 200 MHz) of glycyrrhetinic acid is shown in FIG. 1, and that of the compound obtained is shown in FIG. 2.

(b) The compound having the chemical formula(12) 1.89 g(3.9 mmol) is dissolved in 30 ml of methylene chloride in an atmosphere of nitrogen. Then cool the mixture to −78° C., and 7.9 ml of 1.5M DIBAL in toluene(11.8 mmol) is added at the temperature. Then the mixture is warmed up to room temperature, and stirred overnight. The reaction is terminated by adding 10 ml of water, and the solvent is removed by evaporation. Methylene chloride is added to the residue, and a solid component is broken well. The solution is stirred, and then the solid component remained is removed by filtration. Then methylene chloride is removed by evaporation, and crude alcohol is obtained. The crude alcohol is dissolved in 40 ml of methylene chloride. Two g of MnO$_2$ is added to the solution and the mixture is stirred overnight at room temperature to oxidize the alcohol. The solids formed in the mixture is removed by filtration, and then methylene chloride is removed by evaporation; the residue is applied on preparative TLC(MERK) for purification(separation condition: hexane/ethyl acetate=1/4 (v/v)). This purification gives a novel compound having the following chemical formula(13) with Rf value of 0.7.

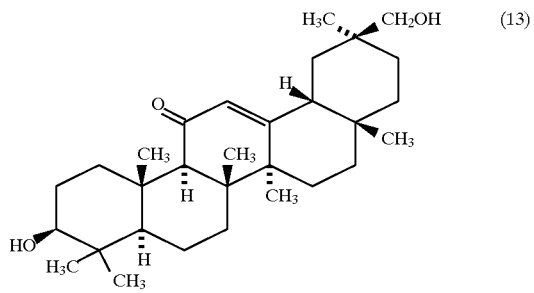

Figure 3:
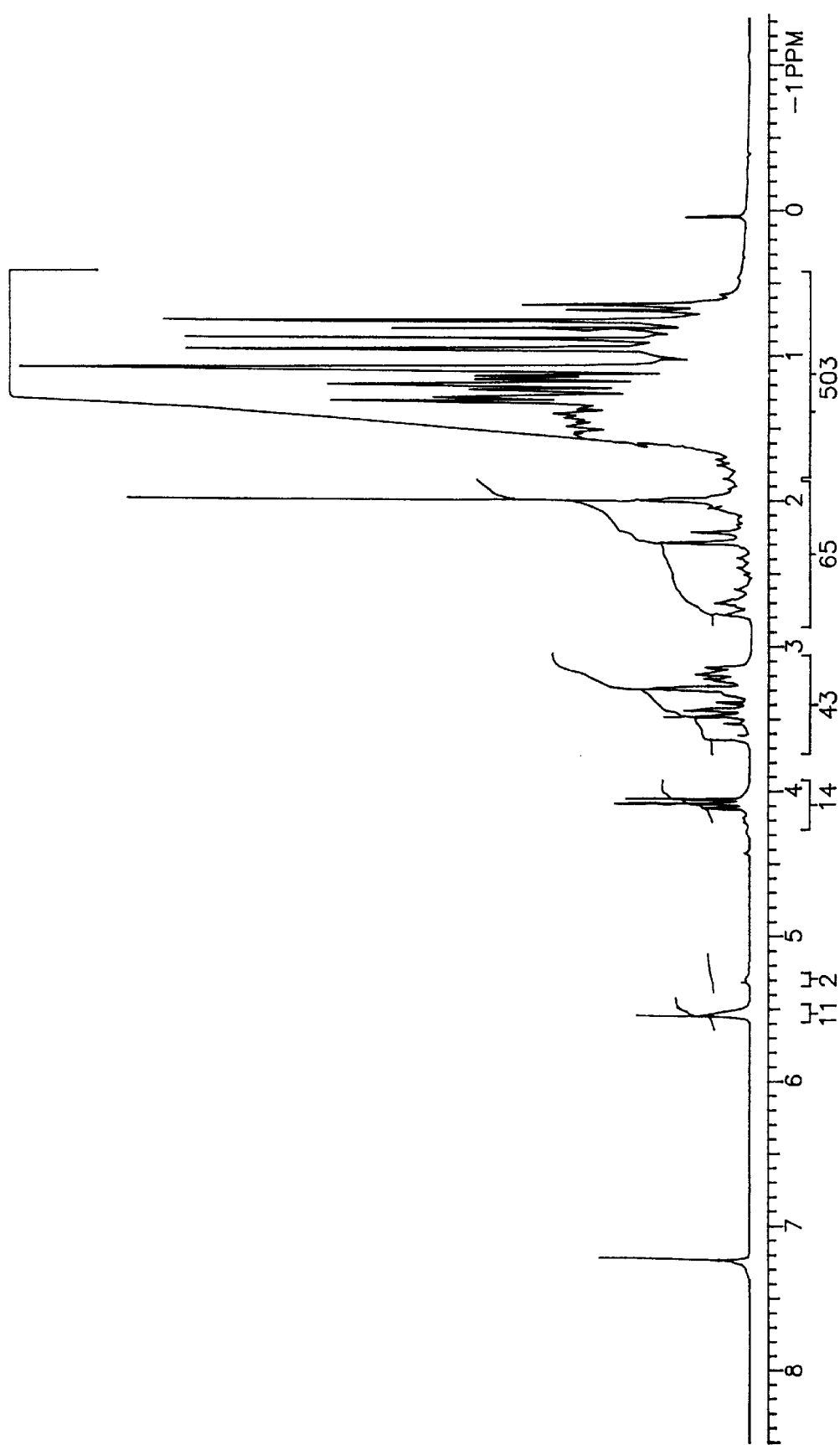
FIG. 3 shows the $^1$H NMR (CDCl$_3$, 200 MHz) spectrum of the compound with chemical formula (13).
Figure 4:
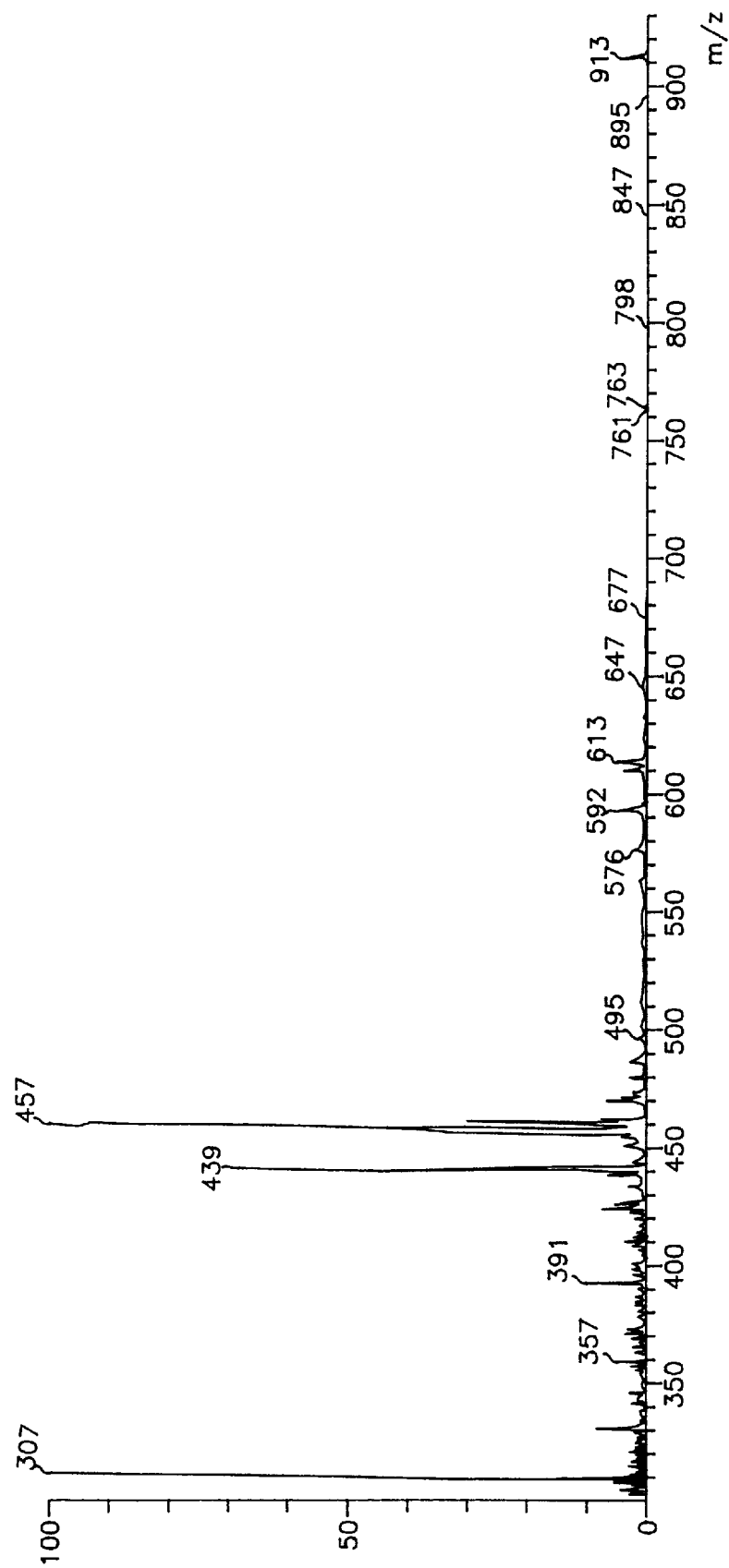
FIG. 4 shows a fast bombard mass spectrum(FAB, positive) of the compound with the chemical formula(13).

The weight of the novel compound obtained is 806 mg, and its yield is 45%. The $^1$H NMR spectrum(CDCl$_3$, 200 MHz) of the novel compound(13) is shown in FIG. 3, and that of FAB(positive) is shown in FIG. 4. The data shown in FIG. 4 reveals that M+1=458.

(c) The compound shown in the formula(13) 806 mg(1.77 mmol) is evaporated with dried pyridine to dry itself(20 ml of pyridine×3 times). Then the dried compound is dissolved in 30 ml of dried pyridine. Nine hundred and sixty mg(283 mmol) of 4,4'-dimethoxytrityl chloride, 20 mg of dimethylaminopyridine(0.16 mmol), and 380 ml of triethylamine(2.8 mmol) are added to the solution. The solution is stirred overnight in an atmosphere of nitrogen at room temperature. The compounds obtained are partitioned by using ethyl acetate-water. The ethyl acetate layer is dried on sodium sulfate anhydride. After that, the ethyl acetate layer is evaporated, and then applied on the silica gel column(elution buffer; methanol/methylene chloride=5/95

(v/v)) to obtain the compound shown in the following chemical formula(19).

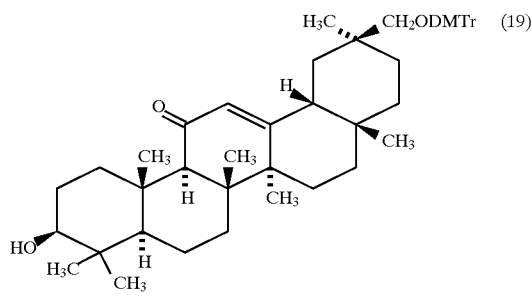

(19)

Figure 5:
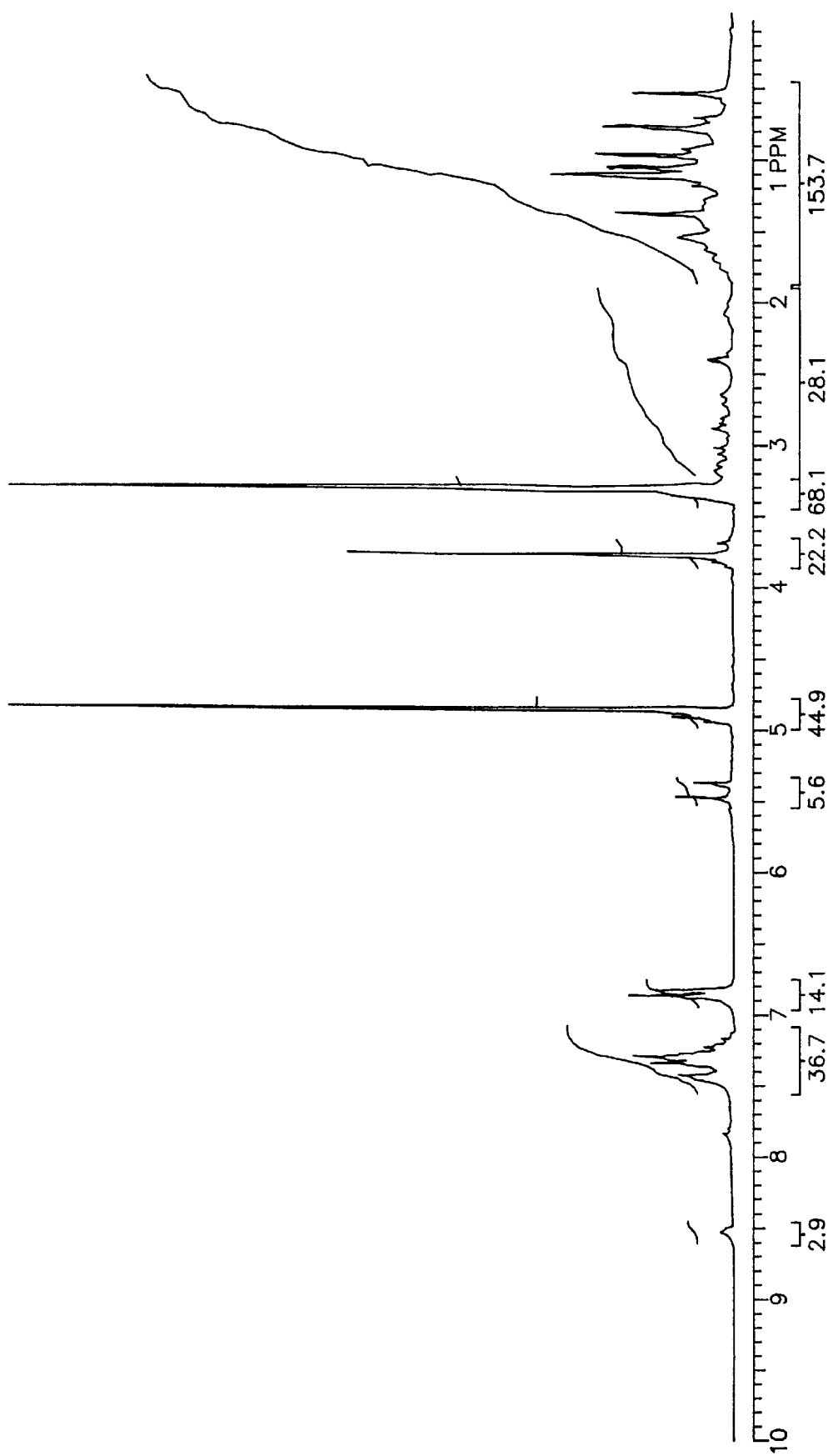
FIG. 5 shows the $^1$H NMR (CDCl$_3$, 200 MHz) spectrum of the compound with the chemical formula(19).

The weight of the compound(19) obtained is 730 mg, and its yield is 54%. The $^1$H NMR spectrum of the novel compound (CDCl$_3$, 200 MHz) is shown in FIG. 5.

(d) Whole amount of the compound shown in the formula (19), 730 mg(0.96 mmol) is evaporated with dried acetonitrile to dry the compound (5 ml×3 times). The dried compound(19) is dissolved in 2 ml of acetonitrile in an atmosphere of nitrogen, after that both 285 mg of 2-cyanoethyl-N, N, N', N'-tetraisopropylphosphoramidite (30,599-5, ALDRICH CHEMICAL) and 2 ml of 1H-tetrazole(0.5M) are added. Then the mixture is reacted overnight at room temperature. After that, the mixture is partitioned by using ethyl acetate-saturated sodium hydrogen carbonate. The ethyl acetate layer is dried on sodium sulfate anhydride. The layer is evaporated to concentrate, and the novel compound having the following chemical formula(20) is obtained.

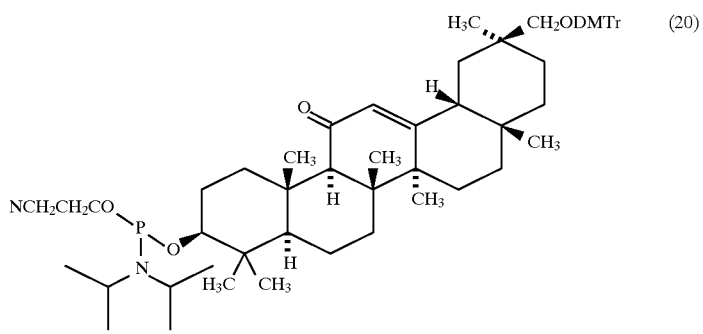

(20)

The weight of the compound obtained is 746 mg, and its yield is 81%.

(e) Whole amount of the compound shown in the formula (20) is dissolved in acetonitrile/methylene chloride (1/1(v/v)) to prepare 0.1M solution. The solution is installed into the DNA synthesizer(381A, ABI) to synthesize DNA according to the known synthesis cycle, which comprises coupling 30 seconds; iodo oxidization 20 seconds; capping 15 seconds; deblocking of DMTr group 100 seconds. Two DNA chains, 5'-d(CTAGGC)— and 3'-d(GATCCG)— which is complementary to 5'-d(CTAGGC)—, are synthe-sized. Since DNAs are protected during their synthesis, such DNAs should be deblocked by using the known protocol and purified by a reverse phase HPLC. The novel nucleic acid compound is thought that it has the following formula(21).

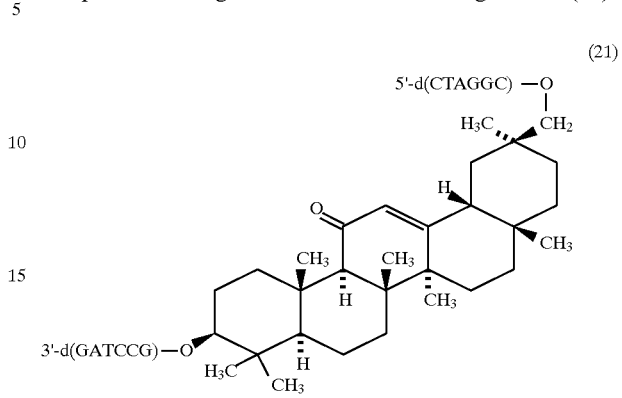

(21)

In order to confirm that the novel compound has the formula(21) as mentioned above, the novel compound is hydrolyzed by using both snake venom phosphatase and alkaline phosphatase. Concretely, the solution containing 0.1 mM of the novel compound (as the base concentration), 50 mM sodium cacodylate (pH 7), 0.03 unit of snake venom phosphatase, and 10 unit of alkaline phosphatase are incubated at 37° C. overnight.

The hydrolyzed compound is analyzed by HPLC. HPLC conditions are as follows.

Column; C$_{18}$

Elution buffer; gradient buffer, 50 mM ammonium formate/acetonitrile (0 to 50%/30 min.).

Flow rate; 1.5 ml/min.

Wavelength; UV 254 nm

Figure 6A:
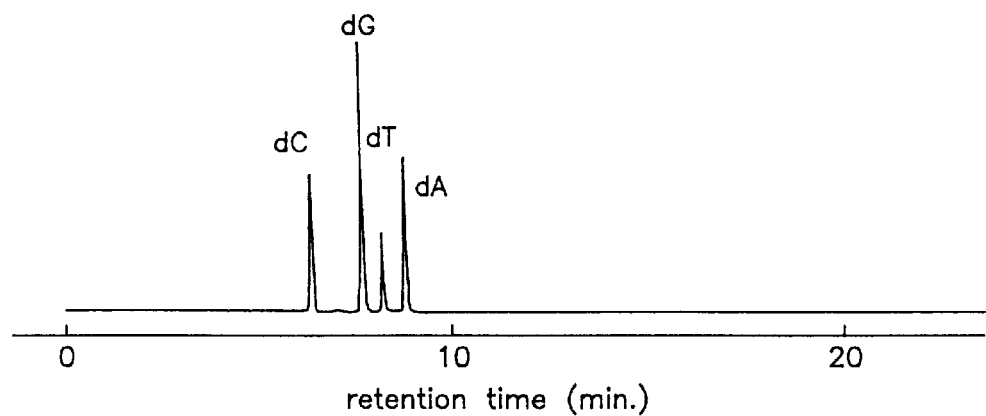
FIG. 6 shows the result given by HPLC analysis of hydrolyzed components of the compound with the chemical formula(21).
Figure 6B:
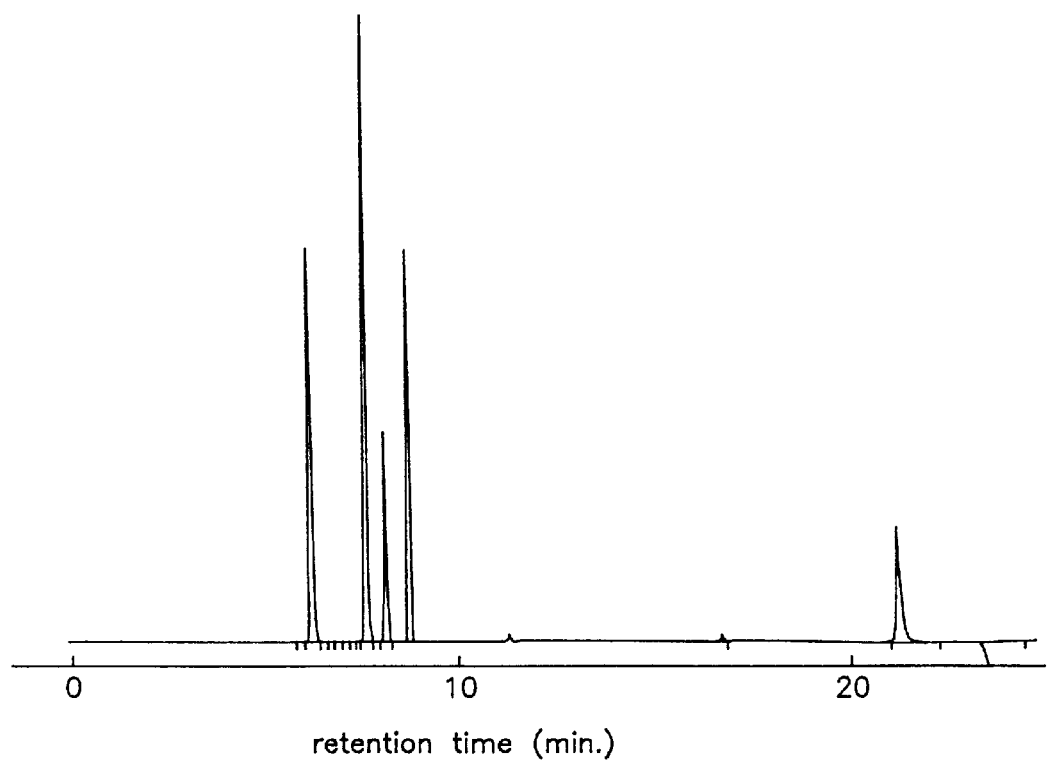

After the analysis, the nucleotide having the sequence CTAGGC(GATCCG) and the compound shown in the following chemical formula(22) are obtained. The data are shown in FIG. 6. The obtained compound is referred to as the compound(22).

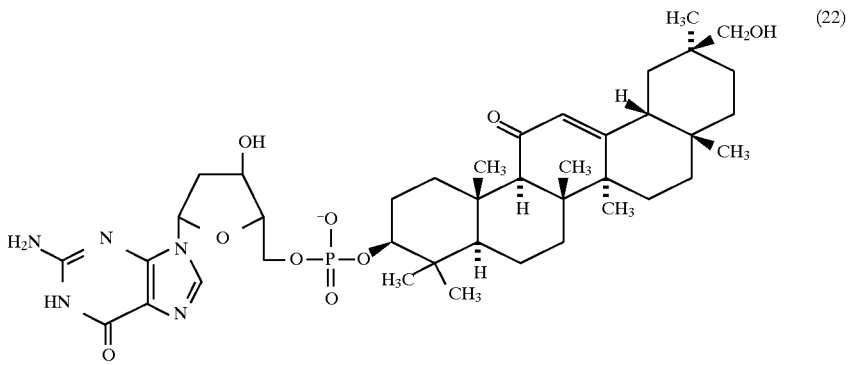

As the standard preparations, deoxycytidine (dC), deoxyguanosine (dG), deoxythimidine (dT), and deoxyadenosine (dA) (YAMASA) are used.

Figure 7:
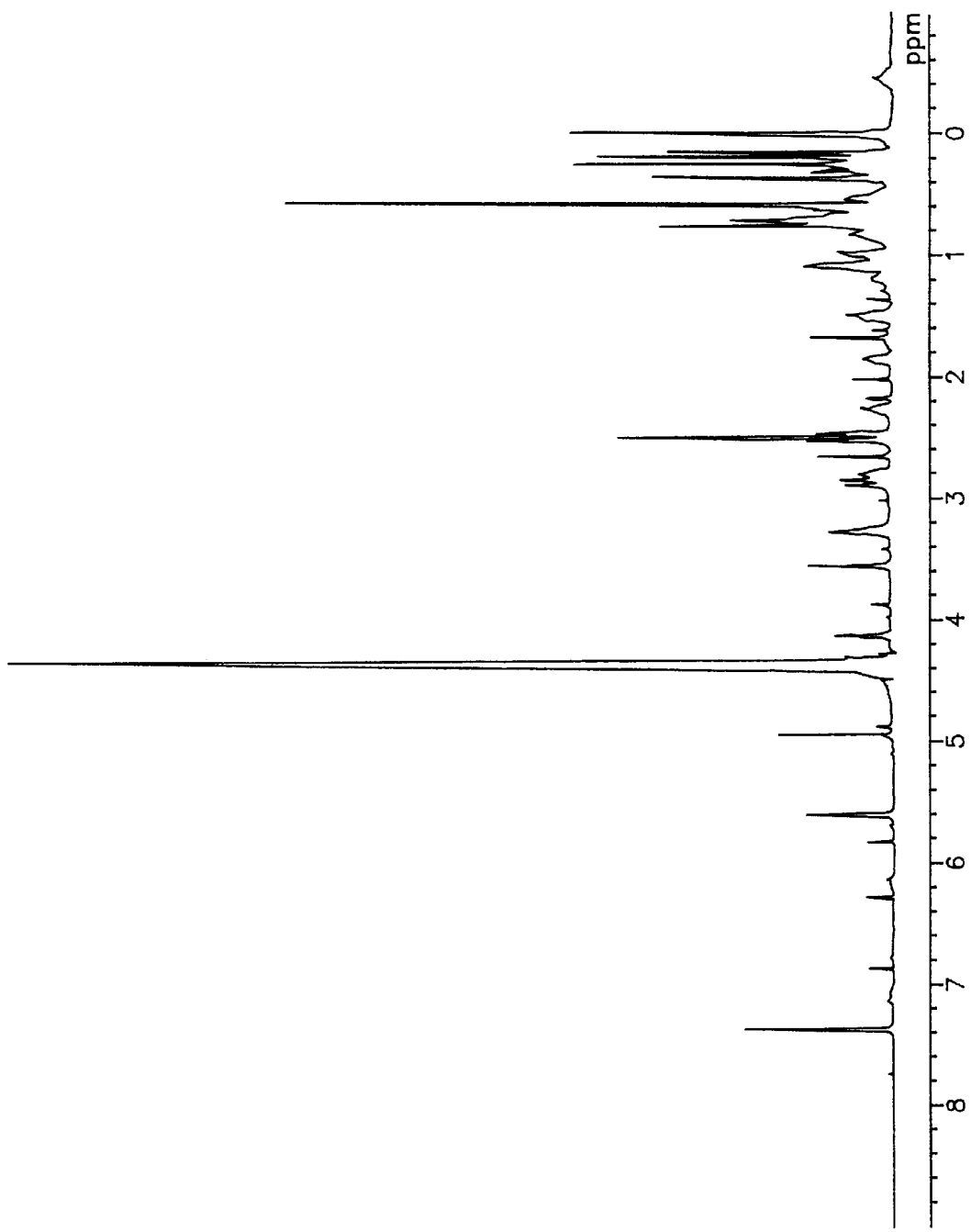
FIG. 7 shows the $^1$H NMR (D$_2$O, 500 MHz) spectrum of the compound with the chemical formula(22).

The $^1$H NMR spectrum (D$_2$O, 500 MHz) of the compound (22) is shown in FIG. 7, and FAB (positive) spectrum of that is shown in FIG. 8. FIG. 8 showed that M+1=787, and M+Na=807. These results demonstrate that the nucleic acid compound obtained has the chemical formula (21), and this compound is referred to as the compound (21).

Furthermore, the melting temperature of the nucleic acid compound (21) is measured under following conditions:

buffer; 10 mM sodium phosphate buffer(pH 7.0)

nucleic acid concentration; 0.05 mM (calculated based on the base concentration)

heating ratio; 2° C./ min.

As a result, the equal mol mixture of 2 hexamers, which correspond to the nucleotide chains bound to the nucleic acid compound(21) showed 20.6° C. as its melting temperature. On the other hand, the nucleic acid compound (21) showed 71.3° C. as that. Accordingly, the results demonstrated that the nucleic acid compound (21) promotes to form the intramolecularly base-paired structure.

(Example 2)

In order to obtain the compound(13), both the steps (a') and (b') are employed instead of both the steps (a) and (b) in EXAMPLE 1.

(a') Three g of aluminum lithium hydride is suspended in 100 ml of anhydrous tetrahydrofuran. Suitable amount of anhydrous tetrahydrofuran containing 2 g of 18β-glycyrrhetinic acid(G1,010-5, ALDRICH CHEMICAL) is added to the solution. The solution is stirred overnight at room temperature. Three ml of water, the same volume of 15% NaOH aqueous solution, and 9 ml of water are added to the solution sequentially in order to decompose both excess aluminum lithium hydride and metal complexes. Then, the solution is concentrated to dryness. The dried compound is crystallized in methanol to obtain the compound shown in the following formula(14). The compound is referred to as the compound(14).

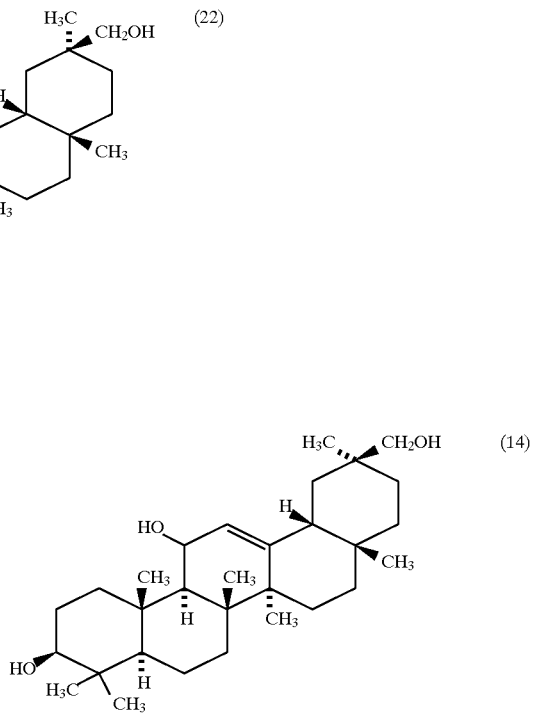

As the compound(14), white crystalline 1.1 g is obtained, and the yield is 57%. The analysis data of the compound(14) are shown in below.

$^1$H NMR (CDCl$_3$, 200 MHz): δ0.81(s, 3H), 0.84(s, 3H), 0.88(s, 3H), 0.98(s, 3H), 1.09(s, 3H), 1.21(s, 3H), 1.37(s, 3H), 0.80–2.05(m, 21H), 3.22(dd, 1H, J=9.6, 5.7 Hz), 3.47 (d, 1H, J=10.8 Hz), 3.54(d, 1H, J=10.8 Hz), 4.28(brs, 1H), 5.29(d, 1H, J=4.2 Hz)

$^{13}$C NMR (CDCl$_3$, 100 MHz): δ15.71, 18.10, 18.70, 19.37, 25.26, 26.38, 27.04, 27.12, 27.37, 28.35, 28.45, 29.55, 32.27, 33.21, 35.55, 36.34, 38.29, 38.68, 38.75, 39.50, 41.86, 42.52, 46.49, 52.48, 55.75, 66.63, 66.74, 79.06, 126.04, 147.97

HR FABMS(positive ion): m/z 459.3838(M+H, 459.3838, calcd for C$_{30}$H$_{51}$O$_3$)

(b') The compound(14) obtained in the step(a), 1.1 g, is dissolved in 200 ml of methylene chloride. Seven g of MnO$_2$ is added to the solution and stirred overnight at room temperature. Then, the solution is filtrated to separate MnO$_2$. The filtrate is concentrated to dryness. After that, the dried compound is crystallized in methanol to obtain the compound shown in the following formula(13).

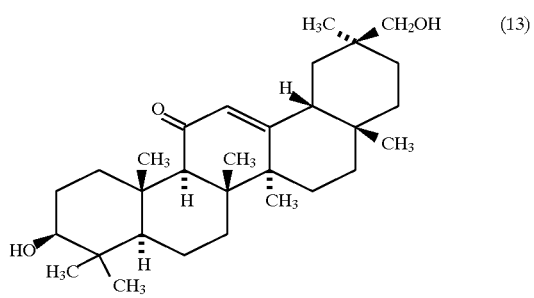

As the compound(13), white crystalline 543 mg is obtained, and the yield is 51%. The analysis data of the compound(13) are shown in below.

$^1$H NMR (CDCl$_3$, 200 MHz): δ0.78(s, 3H), 0.83(s, 3H), 0.89(s, 3H), 0.97(s, 3H), 1.09(s, 3H), 1.10(s, 3H), 1.35(s,

3H), 0.62–2.10(m, 19H), 2.30(s, 1H), 2.75(m, 1H), 3.20(dd, 1H, J=9.8, 5.7 Hz), 3.44(d, 1H, J=11.2 Hz), 3.59(d, 1H, J=11.2 Hz), 5.56(s, 1H)

$^{13}$C NMR (CDCl$_3$, 100 MHz): δ15.56, 16.35, 17.46, 18.69, 23.39, 26.37, 26.70, 27.27, 27.32, 28.07, 28.56, 29.38, 32.28, 32.74, 35.41, 35.92, 37.07, 39.11, 40.29, 43.39, 45.37, 46.98, 50.80, 54.92, 61.76, 66.21, 79.04, 128.31, 169.87, 200.25

HR FABMS(positive ion): m/z 457.3681(M+H, 457.3681, calcd for C$_{30}$H$_{49}$O$_3$)

(Example 3)

In order to obtain the compound(15), the step (b'') is employed instead of the step(b') of the method described in EXAMPLE 2.

(b'') The compound(14) (1.1 g) is dissolved in a mixture of 20 ml of methanol and 1 ml of 1N HCl, and stirred for 1 hr at room temperature. The solution obtained is concentrated to dryness. The resulting compound is crystallized in methanol to obtain the compound shown in the following formula(15).

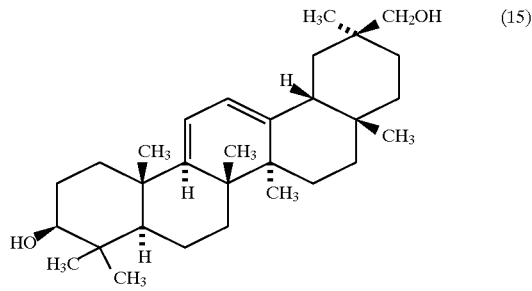

As the compound(15), white crystalline 237 mg is obtained, and the yield is 22%. The analysis data of the compound(15) are shown in below.

$^1$H NMR (CDCl$_3$, 200 MHz): δ0.81(s, 3H), 0.87(s, 3H), 0.98(s, 3H), 1.03(s, 3H), 1.13(s, 3H), 1.16(s, 3H), 1.55(s, 3H), 0.6–2.1(m, 19H), 3.17–3.27(m, 2H), 3.44–3.53(m, 2H), 5.49(d, 1H, J=5.5 Hz), 5.56(d, 1H, J=5.5 Hz)

FABMS(positive ion): m/z 441(M+H, 441, calcd for C$_{30}$H$_{49}$O$_2$)

(Example 4)

In order to study possibility of triple strand formation of the compound shown in the following formula(23),

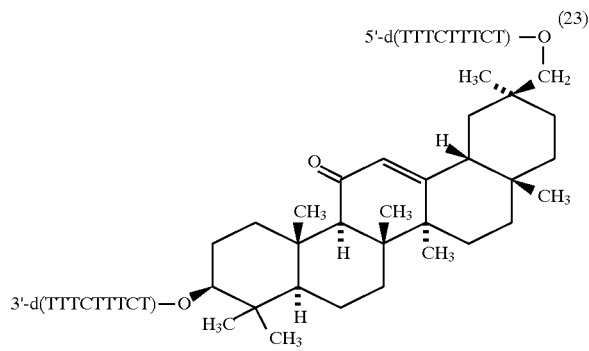

the compound(23) is synthesized by using a similar method described in EXAMPLE 1 except different DNA chains are employed. The compounds and the nucleotide chains shown below are synthesized and purified to study the possibility of their triple strand formation.

Briefly, the compounds and the nucleotide chains are combined herein below, and their interactions are studied.

Combination 1: the nucleic acid compound(23) and the nucleotide chain(24) which has the following DNA sequence.

5'-d(AAAGAAAGA) (24)

Combination 2: the nucleotide chains(24) and (25) which has the following DNA sequences.

5'-d(TCTTTCTTT) (25)

Combination 3: the nucleotide chains(24), (25), and (26) which has the following DNA sequence.

5'-d(TTTCTTTCT) (26)

Wherein, the nucleotide chains(24) has complementary sequence to the 3'-half sequence of the compound(23). The compound(25) has the same DNA sequence as the 3'-half sequence of the compound(23). The nucleotide chain(26) has the same DNA sequence as the 5'-half sequence of the compound(23). The nucleotide chain(26) can form a triple strand by binding to a double strand consisting of the nucleotide chain(24) and that of the 3'-half sequence of compound(23), or the double strand consisting of the nucleic acids(24) and (25).

Such interaction between the nucleic acid compound and the nucleotide chain, or that between the nucleotide chains are studied by UV spectroscopy and circular dichroism. Both UV and the circular dichroism spectra are obtained under the following conditions:

buffer: 10 mM phosphate buffer in the presence of 100 mM NaCl(pH 7.0)

the nucleic acid concentration: 4 μM (based on the concentration of compound or nucleotide chain)

temperature: controlled at a certain temperature

In order to obtain melting temperatures of double or triple strands by UV spectroscopy, we increased or decreased the temperature of sample solution at 0.5° C./minute.

As a result, the melting temperature given by the mixture of the nucleic acid compound(23) and the nucleotide chain (24), which is referred to as the mixture(a), is 27.4° C. In contrast, the melting temperature given by the mixture of the nucleotide chains(24) and (25), which is referred to as the mixture(b), is 18.0° C. The melting temperature given by the mixture of the nucleotide chains(24), (25), and (26), which is referred to as the mixture (c), is 16.8° C. Accordingly, the melting temperature of the mixture(a) is significantly higher than those given by the other mixtures. The results demonstrate that in the mixture(a), the interaction between the nucleic acid compound and the nucleotide chain is stronger than those in either the mixture(b) or(c).

Figure 9:
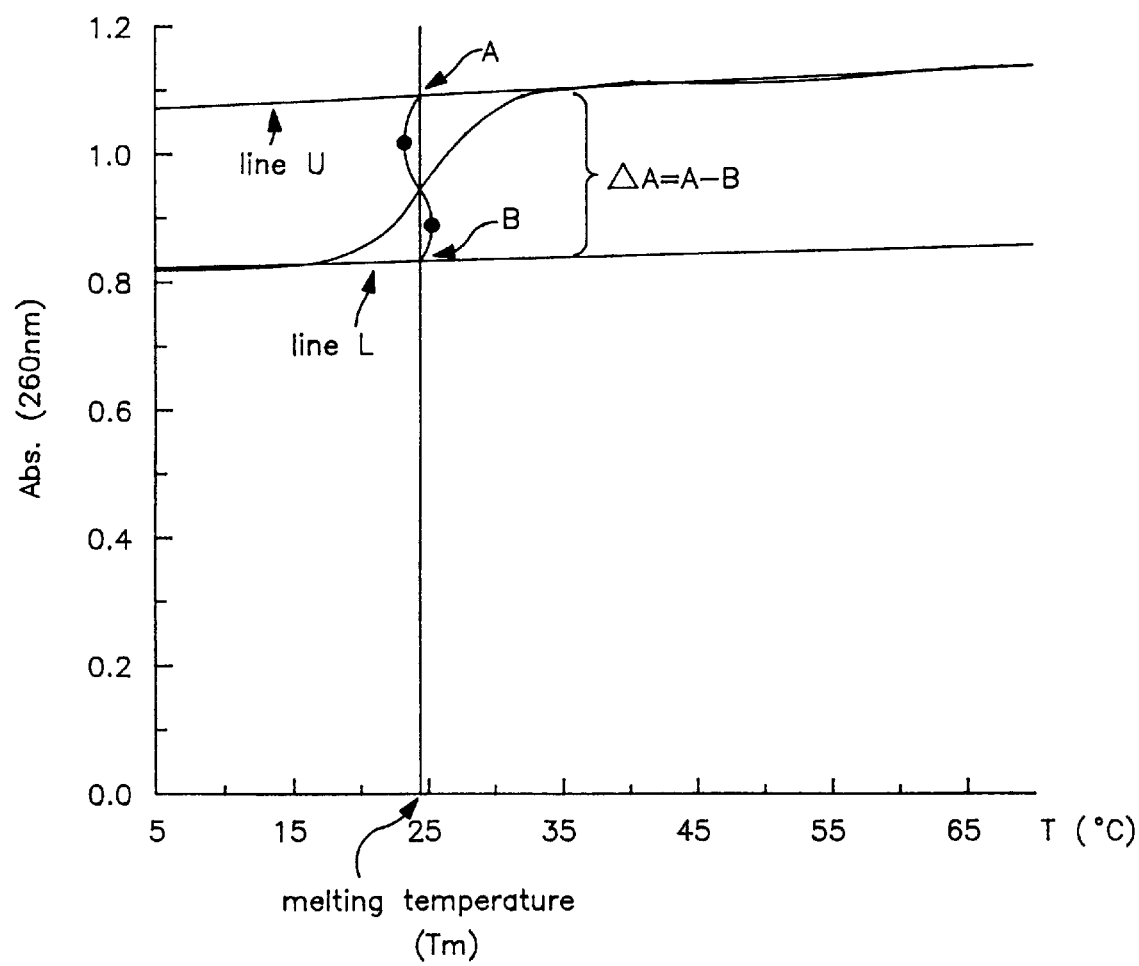
FIG. 9 shows the profile of the absorption intensity ratio (ΔA/A) depends on the temperature in the UV range.

Ultraviolet absorption spectra of the mixtures(a), (b), and (c) change according to temperature of the solution. When double stranded or triple stranded DNA is dissociated into single stranded DNA, absorbance value is increased. In order to know if structure of strand in the mixture is double strand or triple strand, the following procedure is employed. At first, UV spectra of the mixture are measured at a controlled temperature. Since the results showed a sigmoid curve shown in FIG. 9, two values A and B are determined by using the curve as follows. The sigmoid curve comprises two linear part and one slope between them(see FIG. 9). The higher linear part, appeared at higher temperature than the melting temperature of the strand, indicates that only the single stranded DNA is contained in the mixture. The lower linear part, appeared at lower temperature than the melting temperature of the strand, indicates that only the double or triple stranded DNA is contained in the mixture. Since these two linear parts make two lines respectively, they are extrapolated to the melting temperature, and values of absorbance A and B are determined. (The upper line is referred to as the line U, and the lower line is done as the line L. The line U corresponds to single stranded state with random coil. In contrast, the line L corresponds to double stranded or triple stranded state.) Then, ΔA is obtained as the difference of A and B, and ΔA is divided by A to obtain the ratio ΔA/A. It is considered that the ratio reflects which strand (double or triple) is contained in the solution at the lower temperature than the melting temperature, because of physical meaning of the ratio.

The ratio ΔA/A obtained is: 0.188 in the mixture(a), 0.101 in the mixture(b), and 0.097 in the mixture(c). As a result, the ratio obtained from the mixture(a) is significantly higher than that from the mixture(b); however, the ratios obtained from the mixture(b) and (c) do not show significant difference, and they are substantially same. This result indicates that the nucleotide chains in the mixture(a) and (b) are in different states. It is suggested that the nucleotide chains are in double stranded states in the mixture(b) at the temperature lower than the melting temperature. In contrast, it is suggested that the nucleotide chains are in other structure state than double stranded state, and the state is in a increased base stacking.

Figure 10A:
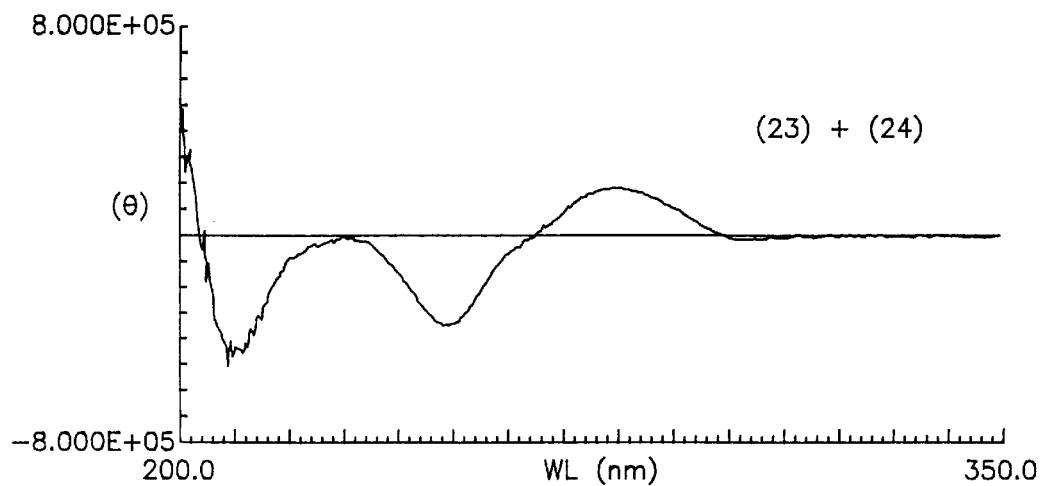
FIG. 10 shows the circular dichroism spectra of several compounds. The upper column shows that given by the mixture of the nucleic compound(23) and the nucleotide chain(24). Medium column shows that given by the mixture of the compound(24) and other nucleotide chain(25). The lower column shows that given by three nucleotide chains (24), (25), and (26) wherein, the Y axis represents the molar ellipticity shown in deg·cm$^2$/dmol.
Figure 10B:
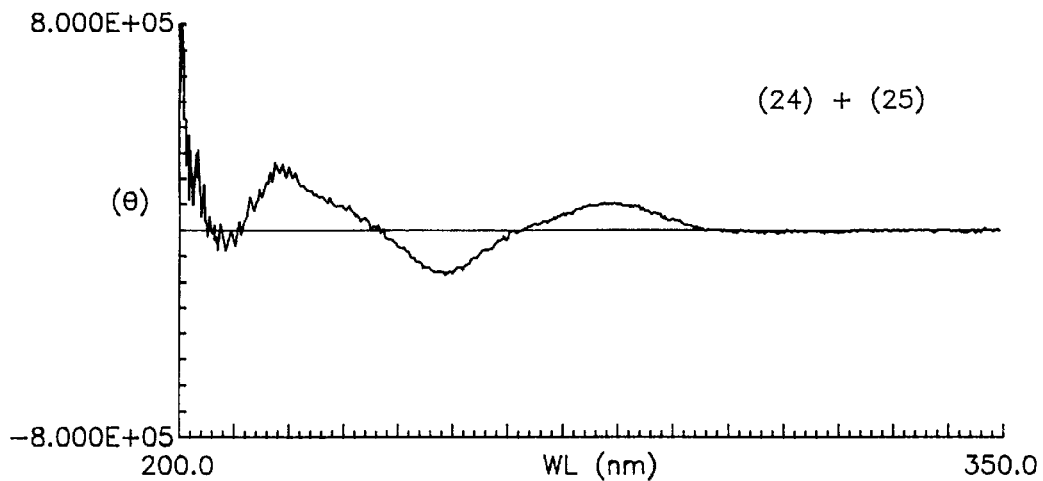
Figure 10C:
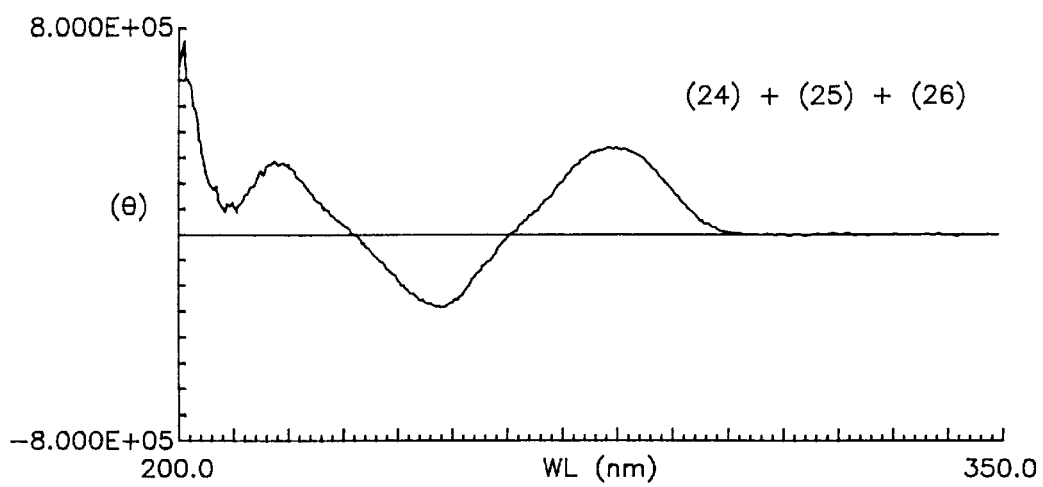

Circular dichroism spectra of the mixture(a), (b) and (c) at 10° C. are shown in FIG. 10. A negative band appears at 211 nm for the mixture(a). However, there is no band around 211 nm in for both the mixture(b) and (c) in FIG. 10. It is known that a negative band appears around 210 nm when a triple strand is formed (D. M. Gray et al., *Methods in Enzymology*, 246:19–34(1995)). Analysis of the circular dichroism spectra based on such two experimental results described above gives the conclusion that the negative band appeared for the mixture(a) is caused by triple strand formation.

In conclusion, according to the above-mentioned experimental results, the nucleic acid compound having the triterpenoid skeleton and such two oligonucleotide chains can form triple strand with the third nucleotide chain. In the triple strand, it is revealed that one of the nucleotide chain of the nucleic acid compound(23) forms Watson-Crick base pair with its complementary nucleotide chain, and another chain of the compound(23) interact with the double strand by forming Hoogsten base pair to give the triple strand.

(Example 5)

(1) Synthesis of nucleotide chains and nucleic compounds for studying their incorporation into cells.

The compound shown in the following formula(27) is synthesized by using a similar method as described in EXAMPLE 1 except different DNA chains are used, and then they are purified, and referred to as the compound(27).

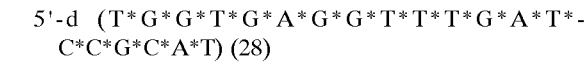
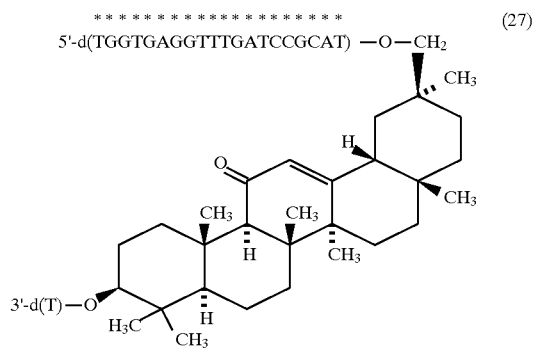

*: phosphorothioate bond

In synthesis of (27), Beaucage reagent([3H]1,2-benzodithiol-3-one-1,1-dioxide) is employed to obtain the compound with phosphorothioate bond (designated as * in (27)), instead of usual phosphodiester bond.

Furthermore, compounds shown in the following formula (28) is synthesized to compare with (27) for incorporation into cells.

5'-d (T*G*G*T*G*A*G*G*T*T*T*G*A*T*-C*C*G*C*A*T) (28)

*: phosphorothioate bond.

The nucleotide sequence described above has only phosphorothioate bonds instead of phosphodiester bonds.

The nucleic acid compound(27) and the nucleotide chain (28) obtained are labeled at their 5'-termini by using both T4 polynucleotide kinase and [γ-$^{32}$P]ATP (10 mCi/ml) to study incorporation into cells.

(2) The incorporation of the nucleotide chain and the nucleic acid compound into A549 cells.

Human lung carcinoma cell line A549 is employed. The cells are inoculated into 96 well microtiter plates, and cultured in DMEM supplemented with 10% FCS at 37° C. for 3 days in the presence of 5% $CO_2$. After three days, the cells are confluent(about 1×10$^5$ cells/well), and washed with serum-free medium, OPTI-MEM.

The labeled and unlabeled nucleic acid compound(27) are mixed and added to OPTI-MEM so as to their total concentration is 1 μM to prepare the incorporation medium. Similarly, both labeled and unlabeled nucleotide chain (28) are mixed and added to OPTI-MEM so as to their total concentration is 1 μM to prepare the incorporation medium. The concentration 1 μM corresponds to 5.5×10$^4$ cpm/well. Then, the plate is incubated at 37° C. in the presence of 5% $CO_2$ for 4 hours.

Then the medium is removed, and the cells are washed with phosphate buffered saline(PBS). Then, the cells are treated with 0.05% trypsin/0.53 mM EDTA. By this treatment, the cells are dissociated from 96 well plate and the nucleic acid compounds associated on the cell surface are also removed. This solution containing cells is transferred to microtubes, and centrifuged at 1,500 rpm for 10 minutes. Their supernatants are removed. The cells collected in the bottom of the microtubes are dissolved in 1% SDS solution. Two hundred μl of the SDS solution is transferred into vials, and the amount of the above-mentioned compound incorporated into the cells are determined by using liquid scintillation.

The amounts of the above-mentioned compounds(27) and (28) incorporated are shown as the ratio when the amount of the nucleotide chain(28) incorporated equals to 1. As a result, the incorporation ratio of the compound(28) is 2.1±0.6. This demonstrate that the incorporation of the compound(27) is significantly higher than its reference.

In conclusion, the result demonstrate that the nucleic acid compounds having triterpenoid skeleton(27), which is the compound of the present invention, are easily incorporated into such cells. The result also demonstrate that the compound of the present invention has improved cell membrane permeability.

We claim:

1. A nucleic acid compound which has a moiety of a non-nucleic acid structure with a ring skeleton to which two functional groups are bound with a fixed conformation and are able to point to substantially the same direction, and a moiety of a pair of nucleotide chains which are bound to the functional groups.

2. A nucleic acid compound according to claim 1, wherein said a pair of nucleotide chains are complementary to each other.

3. A nucleic acid compound according to claim 1, wherein the distance between said functional groups on said non-nucleic acid compound is 0.6 to 1.4 nm.

4. A nucleic acid compound according to claim 1, wherein one nucleotide chain of said pair of nucleotide chains is complementary to a third nucleotide chain to form a double strand, and the other chain of said pair of nucleotide chains forms a triple strand with the double strand.

5. A nucleic acid compound according to claim 1, wherein said non-nucleic acid skeleton is a triterpenoid skeleton.

6. A nucleic acid compound according to claim 1, wherein said non-nucleic acid skeleton is shown in chemical formula (1);

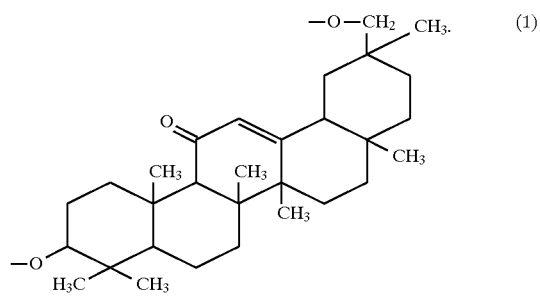

7. A nucleic acid compound according to claim 1, wherein said non-nucleic acid skeleton is shown in chemical formula (2);

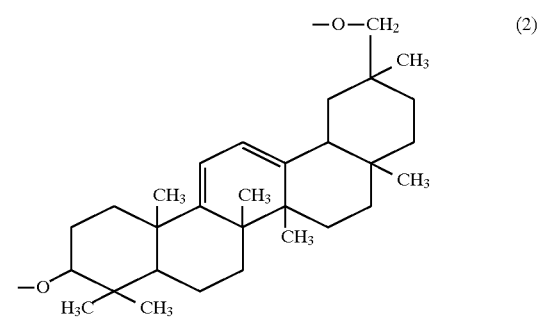

8. A synthetic method for making a nucleic acid compound, said method comprising:
(a) introducing a protecting group into one hydroxyl group of non-nucleic acid compound with a ring skeleton to which two hydroxyl groups are bound with a fixed conformation and are able to point to substantially the same direction;
(b) binding the other hydroxyl group of said compound to the first nucleotide chain of a pair of nucleotide chains;
(c) removing said protecting group of the compound; and
(d) binding the deblocked hydroxyl group of the compound to the second nucleotide chain of said pair of nucleotide chains.

9. A synthetic method for a nucleic acid compound according to claim 8 wherein said nucleotide chains are complementary to each other.

10. A synthetic method for a nucleic acid compound according to claim 8, wherein one of nucleotide chains added is complementary to a third nucleotide chain to form double strand, and the other nucleotide chain can form triple strand with the double strand.

11. A synthetic method for said nucleic acid compound according to claim 8, wherein the distance between said functional groups on said non-nucleic acid compound is 0.6 to 1.4nm.

12. A synthetic method according to claim 8, wherein said nucleotide chains are modified by substitution of phosphoramidite or thiophosphite diesters in place of one or more phosphodiester moieties.

13. A synthetic method for said nucleic acid compound according to claim 8, wherein said non-nucleic acid compound is a triterpenoid compound.

14. A synthetic method for said nucleic acid compound according to claim 8, wherein said non-nucleic acid compound is a compound having a skeleton shown in chemical formula(1):

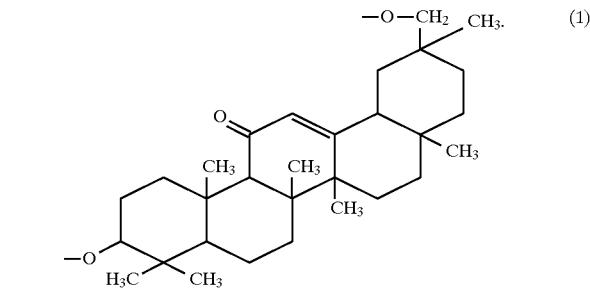

15. A synthetic mehtod for said nucleic acid compound according to claim 8, wherein said non-nucleic acid compound is a compound having a skeleton shown in chemical formula(2);

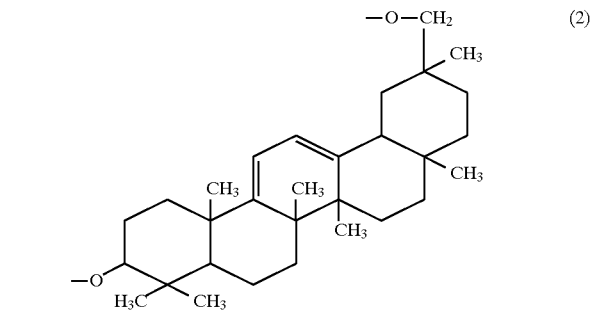

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

C T A G G C      6

( 2 ) INFORMATION FOR SEQ ID NO:2:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

G A T C C G      6

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

A A A G A A A G A      9

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

T C T T T C T T T      9

( 2 ) INFORMATION FOR SEQ ID NO:5:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

T T T C T T T C T      9

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (xi) SEQUENCE DESCRIPTION: SEQ ID NO:6:

TGGTGAGGTT TGATCCGCAT                                                                                                    20